(12) United States Patent
Oda

(10) Patent No.: US 9,158,004 B2
(45) Date of Patent: Oct. 13, 2015

(54) RADIATION DETECTION DEVICE, RADIOGRAPHIC IMAGE CAPTURE DEVICE, RADIATION DETECTION METHOD AND PROGRAM STORAGE MEDIUM

(71) Applicant: FUJIFILM Corporation, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 236 days.

(21) Appl. No.: 13/711,505

(22) Filed: Dec. 11, 2012

(65) Prior Publication Data

US 2013/0206998 A1 Aug. 15, 2013

(30) Foreign Application Priority Data

Feb. 13, 2012 (JP) .................................. 2012-028746

(51) Int. Cl.
| | | |
|---|---|---|
| *G01T 1/17* | (2006.01) | |
| *A61B 6/00* | (2006.01) | |
| *H04N 5/32* | (2006.01) | |
| *H04N 5/361* | (2011.01) | |

(52) U.S. Cl.
CPC . *G01T 1/17* (2013.01); *A61B 6/548* (2013.01); *H04N 5/32* (2013.01); *H04N 5/361* (2013.01)

(58) Field of Classification Search
CPC ....................................................... G01T 1/17

USPC .................. 250/393, 394, 370.08, 370.09
See application file for complete search history.

(56) References Cited

U.S. PATENT DOCUMENTS

| | | | |
|---|---|---|---|
| 7,768,002 B2 * | 8/2010 | Kitamura et al. ................ 257/40 |
| 2006/0017009 A1 * | 1/2006 | Rink et al. .................. 250/484.5 |
| 2012/0091353 A1 * | 4/2012 | Enomoto ................. 250/370.08 |

FOREIGN PATENT DOCUMENTS

| | | | |
|---|---|---|---|
| JP | 2009-212389 A | 9/2009 |
| JP | 2011-177356 A | 9/2011 |

\* cited by examiner

*Primary Examiner* — David Porta
*Assistant Examiner* — Meenakshi Sahu
(74) *Attorney, Agent, or Firm* — McGinn IP Law Group, PLLC.

(57) ABSTRACT

A radiation detection device includes a radiation detection sensor, a first integration section, a second integration section and a determination section. The first integration section obtains a first integration value by integrating values expressed by signals output from the sensor over a predetermined period of time. The second integration section obtains a second integration value by integrating amounts of change per specific time duration in values expressed by the signals output from the sensor over the predetermined period of time. The determination section determines whether or not radiation has been detected by the sensor based on a ratio of the first integration value to the second integration value.

17 Claims, 19 Drawing Sheets

FIG.15

INITIAL DATA INPUT SCREEN    111

PLEASE INPUT SUBJECT NAME, IMAGING TARGET SITE,
IMAGE CAPTURE ORIENTATION AND EXPOSURE CONDITIONS

NAME:
IMAGING TARGET SITE:
IMAGE CAPTURE ORIENTATION
EXPOSURE CONDITIONS
    VALVE VOLTAGE
    VALVE CURRENT

COMPLETE

IMAGING PIXEL

DETECTION PIXEL

IMAGING PIXEL

DETECTION PIXEL

RADIATION DETECTION DEVICE, RADIOGRAPHIC IMAGE CAPTURE DEVICE, RADIATION DETECTION METHOD AND PROGRAM STORAGE MEDIUM

CROSS-REFERENCE TO RELATED APPLICATION

This application claims priority under 35 USC 119 from Japanese Patent Application No. 2012-028746 filed on Feb. 13, 2012, the disclosure of which is incorporated by reference herein.

BACKGROUND OF THE INVENTION

1. Field of the Invention

The present invention relates to a radiation detection device, a radiographic image capture device, a radiation detection method and program storage medium, and in particular to a radiation detection device, a radiation detection method and program storage medium that detects initiation of irradiation of radiation, and a radiographic image capture device that captures a radiographic image expressing radiation passed through a subject.

2. Description of the Related Art

Recently, radiation detectors such as Flat Panel Detectors (FPDs) are being implemented in which a radiation sensitive layer is disposed on a Thin Film Transistor (TFT) active matrix substrate and with which radiation can be converted directly into digital data. Radiographic image capture devices that employ such radiation detectors and can capture radiographic images expressing irradiated radiation are also being implemented. Radiation conversion methods used by radiation detectors employed in such radiographic image capture devices include indirect conversion methods, in which radiation is first converted into light with a scintillator and then the converted light is converted into electric charge with a semiconductor layer such as a photodiode, or direct conversion methods in which radiation is converted into electric charge with a semiconductor layer such as amorphous selenium. There are various materials that may be used in the semiconductor layer for each method.

In such radiographic image capture devices, if the radiographic image capture device itself can detect states such as initiation of radiation irradiation, termination of radiation irradiation, and an irradiated amount of radiation, it becomes unnecessary to connect an image capture control device (referred to as a console) that performs overall control of the radiographic image capture device and the radiation source to the radiation source. Such a configuration is preferable from the perspective of simplifying the system configuration and simplifying control by the image capture control device.

A radiation detection method utilizing a histogram is disclosed in Japanese Patent Application Laid-Open (JP-A) No. 2011-177356 as technology related to such types of radiographic image capture devices capable of detecting the irradiation state of radiation. In this technology, initiation of radiation irradiation is determined based on a frequency distribution of difference data obtained by voting difference data between data of adjacent radiation detection elements on a detection section onto a single histogram for each frame.

However, in the technology disclosed in JP-A No. 2011-177356, since radiation is detected by employing difference data between data for adjacent radiation detection elements, the value of the difference data gets smaller as the irradiation amount of radiation gets smaller. Therefore, in this technology the detection precision of radiation decreases as the irradiation amount of radiation gets smaller.

SUMMARY

In consideration of the above circumstances, the present invention provides a radiation detection device, a radiographic image capture device, a radiation detection method and a program storage medium capable of detecting radiation at high precision irrespective of the irradiation amount of radiation.

A first aspect of the present invention is a radiation detection device including: a sensor that detects radiation; a first integration section that obtains a first integration value by integrating values expressed by signals output from the sensor over a predetermined period of time; a second integration section that obtains a second integration value by integrating amounts of change per specific time duration in values expressed by the signals output from the sensor over the predetermined period of time; and a determination section that determines whether or not radiation has been detected by the sensor based on a ratio of the first integration value to the second integration value.

According to the first aspect, the values expressed by the signal output from the sensor for radiation detection over a predetermined period of time are integrated by the first integration section, and the amounts of change per specific time duration in values expressed by the signal output from the sensor over the predetermined period of time are integrated by the second integration section.

Determination is made in the determination section as to whether or not radiation has been detected by the sensor based on the ratio of the first integration value obtained by the first integration section and the second integration value obtained by the second integration section.

In cases in which shock is imparted or extraneous noise from an electromagnetic field is added to the radiographic image capture device, as shown in FIG. 10 and FIG. 11, the values (detection values) expressed by the signal output from the sensor for radiation detection fluctuate and oscillate with a comparatively large amplitude. In contrast, no such oscillation occurs in cases in which radiation is irradiated in states where no such external disturbance occurs, as shown in FIG. 12 and FIG. 13.

Therefore, in the first aspect, the integration value (first integration value) of the values expressed by the signal output from the sensor for radiation detection over the predetermined period of time and the integration value (second integration value) of the amounts of change per specific time duration in values expressed by the signal output from the sensor over the predetermined period of time are employed in the determination as to whether or not radiation has been detected by the sensor. Radiation can accordingly be detected with higher precision.

Further, since the ratio of the first integration value to the second integration value is employed in the determination as to whether or not radiation has been detected, radiation detection can be performed with high precision irrespective of the irradiation amount of radiation in comparison to the conventional technology that detects radiation employing difference data between data for adjacent radiation detection elements (pixels).

According to the present aspect, radiation can be therefore be detected with high precision irrespective of the irradiation amount of radiation.

In the present aspect, configuration may be made such that the determination section determines that radiation has been detected by the sensor if the ratio of the first integration value to the second integration value is equal to or greater than a threshold value. Thereby, the radiation detection can be performed more simply.

In the present aspect, configuration may be made such that: the sensor includes a conversion portion that converts irradiated radiation into electric charge and a switching element that is switched ON when reading electric charge generated by the conversion portion; the radiation detection device further includes an offset correction section that performs offset correction on the first integration value and the second integration value to reduce one or more of the influence of electric charge arising from dark current occurring in the conversion portion or the influence of switching noise that occurs when the switching element is switched; and the determination section performs the determination using the first integration value and the second integration value on which the offset correction has been performed. Radiation can accordingly be detected with higher precision.

The present aspect may further include a fixed noise correction section that performs fixed noise reduction correction on the first integration value and the second integration value to reduce the influence of fixed noise that inherently occurs according to a position of the sensor, and the determination section may perform the determination using the first integration value and the second integration value on which the fixed noise reduction correction has been performed. Radiation can accordingly be detected with higher precision.

In the present aspect, configuration may be made such that the values subject to integration by the first integration section and the second integration section are values within a predetermined range. Radiation can accordingly be detected with higher precision since the influence of factors such as unexpected noise can be reduced.

A second aspect of the present invention is a radiographic image capture device including: the radiation detection device of the first aspect; a radiographic image capture panel including plural radiographic image capture pixels, each including a conversion portion that converts irradiated radiation into electric charge and a switching element that is switched ON when reading electric charge generated by the conversion portion; and a controller that controls the radiographic image capture panel to perform radiographic image capture if it is determined by the determination section of the radiation detection device that radiation has been detected by the sensor.

According to the second aspect, determination as to whether or not radiation has been detected is made by the determination section of the radiographic image detection device of the first aspect. Radiographic image capture is performed with the radiographic image capture panel including the plural radiographic image capture pixels each including a conversion portion that converts irradiated radiation into electric charge and a switching element that is switched ON when reading electric charge generated by the conversion portion.

In the present aspect, the controller effects control such that the radiographic image capture panel performs radiographic image capture if it is determined by the determination section of the radiation detection device that radiation has been detected by the sensor.

According to the second aspect, radiation detection can be performed with high precision irrespective of the irradiation amount of radiation, similarly to the radiation detection device of the first aspect, since the radiation detection device of the first aspect is included.

In the second aspect, configuration may be made such that the sensor of the radiation detection device is provided at the radiographic image capture panel. Accordingly, there is no need of a region that is necessary if the sensor is provided at positions other than the radiographic image capture panel.

In the second aspect, configuration may be made such that: the sensor includes plural radiation detection pixels, each including the conversion portion; the radiographic image capture panel includes: the plural radiographic image capture pixels and the plural radiation detection pixels arrayed in a matrix formation, the matrix formation having plural arrays including an array that includes at least one of the radiation detection pixels; and plural signal lines, each of which is connected to the pixels arrayed in a different one of the plural arrays; the first integration section integrates values, representing electric charge read from a signal line of the plural signal lines provided for the array that includes at least one of the radiation detection pixels, as the first integration value; and the second integration section integrates amounts of change per specific time duration in values, representing electric charge read from the signal line of the plural signal lines provided for the array that includes at least one of the radiation detection pixels, as the second integration value. Accordingly, the present aspect can be readily implemented using existing radiographic image capture panels.

In the second aspect, configuration may be made such that a portion of the plural radiographic image capture pixels is used as the sensor. Accordingly, there is no need to provide an additional sensor for radiation detection, enabling the present aspect to be readily implemented.

In the second aspect, configuration may be made such that the switching element of the sensor is shorted across switching terminals. Accordingly, the sensor can be easily configured using existing manufacturing processes.

A third aspect of the present invention is a radiation detection method including: acquiring a first integration value by integrating values expressed by signals output from a sensor for radiation detection over a predetermined period of time; acquiring a second integration value by integrating amounts of change per specific time duration in values expressed by the signals output from the sensor over the predetermined period of time; and determining whether or not radiation has been detected by the sensor based on a ratio of the first integration value to the second integration value.

Since the third aspect operates similarly to the first aspect, radiation detection can be performed with high precision irrespective of the irradiation amount of radiation.

A fourth aspect of the present invention is a non-transitory storage medium stored with a program that causes a computer to execute radiation detection processing, the radiation detection processing including: acquiring a first integration value by integrating values expressed by signals output from a sensor for radiation detection over a predetermined period of time; acquiring a second integration value by integrating amounts of change per specific time duration in values expressed by the signals output from the sensor over the predetermined period of time; and determining whether or not radiation has been detected by the sensor based on a ratio of the first integration value to the second integration value.

Since the fourth aspect operates similarly to the first aspect, radiation detection can be performed with high precision irrespective of the irradiation amount of radiation.

According to each of the above aspects, radiation detection can be performed with high precision irrespective of the irradiation amount of radiation.

BRIEF DESCRIPTION OF THE DRAWINGS

Exemplary embodiments of the present invention will be described in detail based on the following figures, wherein:

FIG. 15 is a schematic diagram illustrating an example of an initial data input screen according to an exemplary embodiment;

DETAILED DESCRIPTION OF THE INVENTION

Hereinafter, an example of a case in which an embodiment is applied to a radiology information system, which is a system that as a whole manages information handled in a radiology department in a hospital, will be described.

Figure 1:
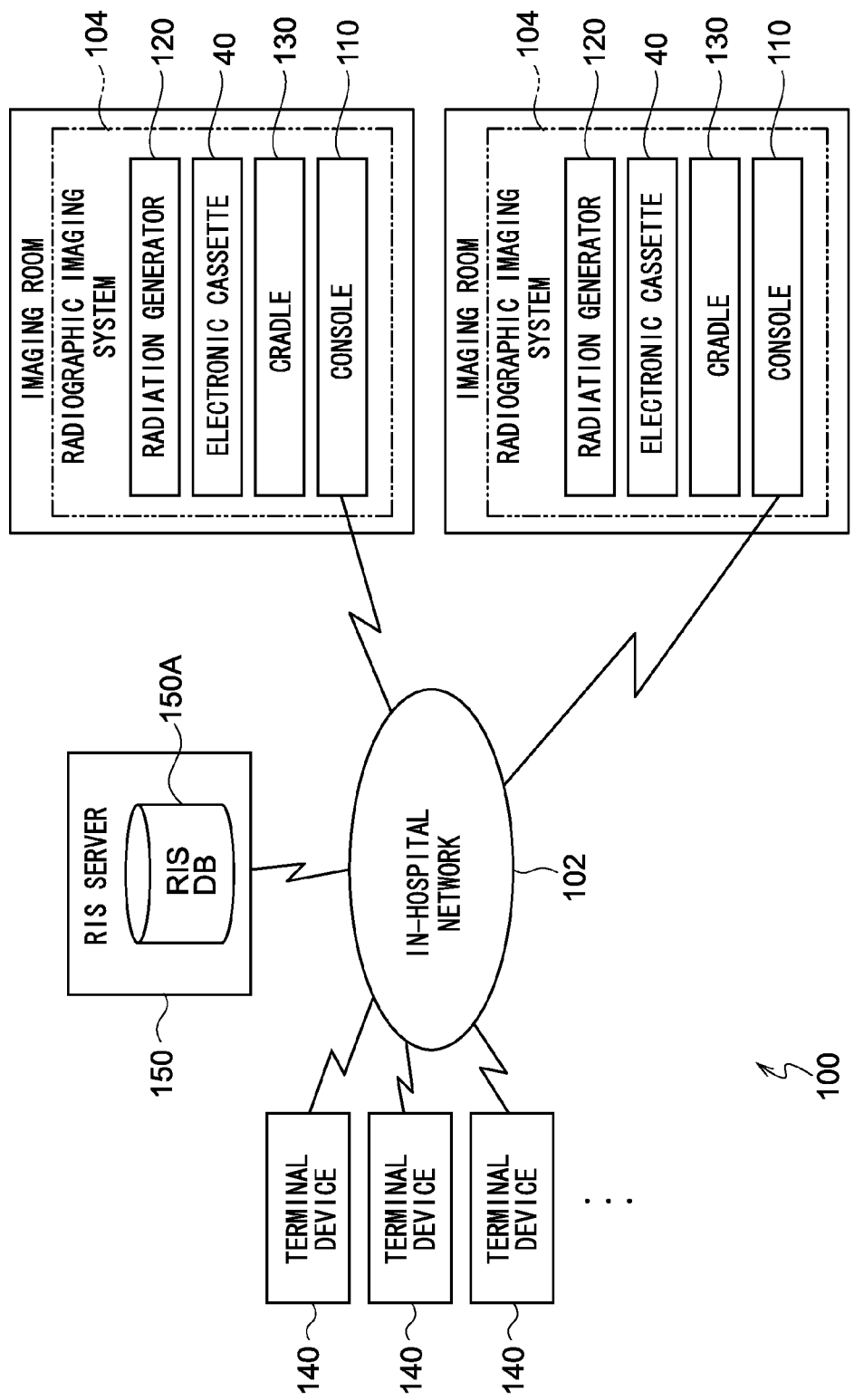
FIG. 1 is a block diagram illustrating a configuration of a radiology information system according to an exemplary embodiment.

First, the configuration of a radiology information system (RIS) 100 pertaining to the present exemplary embodiment will be described with reference to FIG. 1.

The RIS 100 is a system for managing information such as medical service appointments and diagnostic records in a radiology department and configures part of a hospital information system (HIS).

The RIS 100 has plural imaging request terminal devices (terminal devices) 140, an RIS server 150, and radiographic image capture systems (the imaging system) 104. The imaging systems 104 are installed in individual radiographic imaging rooms (or operating rooms) in a hospital. The RIS 100 is configured as a result of the terminal devices 140, the RIS server 150, and the imaging systems 104 being connected to an in-hospital network 102 configured by a wired or wireless local area network (LAN). The RIS 100 configures part of the HIS disposed in the same hospital, and an HIS server (not shown in the drawings) that manages the entire HIS is also connected to the in-hospital network 102.

The terminal devices 140 are for doctors or radiologic technologists to input and browse diagnostic information and facility reservations. Radiographic imaging requests and imaging reservations are also made via the terminal devices 140. Each of the terminal devices 140 includes a personal computer having a display device, and the terminal devices 140 are made capable of intercommunicating with the RIS server 150 via the in-hospital network 102.

The RIS server 150 receives imaging requests from each of the terminal devices 140 and manages radiographic imaging schedules in the imaging systems 104. The RIS server 150 includes a database 150A.

The database 150A includes: information relating to patients (subjects), such as attribute information (names, sexes, dates of birth, ages, blood types, body weights, patient identifications (IDs), etc.), medical histories, consultation histories, radiographic images that have been captured in the past, etc.; information relating to later-described electronic cassettes 40 used in the imaging systems 104, such as identification numbers (ID information), models, sizes, sensitivities, dates of first use, numbers of times used, etc.; and environment information representing the environments in which radiographic images are captured using the electronic cassettes 40—that is, the environments in which the electronic cassettes 40 are used (e.g., radiographic imaging rooms, operating rooms, etc.).

The imaging systems 104 capture radiographic images as a result of being operated by the doctors or the radiologic technologists in response to an instruction from the RIS server 150. Each of the imaging systems 104 is equipped with a radiation generator 120 that applies a dose of radiation X (see FIG. 7) according to exposure conditions from a radiation source 121 (see FIG. 9) to a subject. Further, each of the imaging systems 104 is equipped with an electronic cassette 40, a cradle 130, and a console 110. The electronic cassette 40 has a built-in radiation detector 20 (see FIG. 7) that absorbs the radiation X that has passed through an imaging target site of the subject, generates electric charges, and creates image information representing a radiographic image on the basis of the generated electric charge quantity. The cradle 130 charges a battery that is built into the electronic cassette 40. The console 110 controls the electronic cassette 40 and the radiation generator 120.

The console 110 acquires various types of information (data) stored in the database 150A from the RIS server 150, stores the data in a later-described HDD 116 (see FIG. 9), and uses the data as needed to control the electronic cassette 40 and the radiation generator 120.

Figure 2:
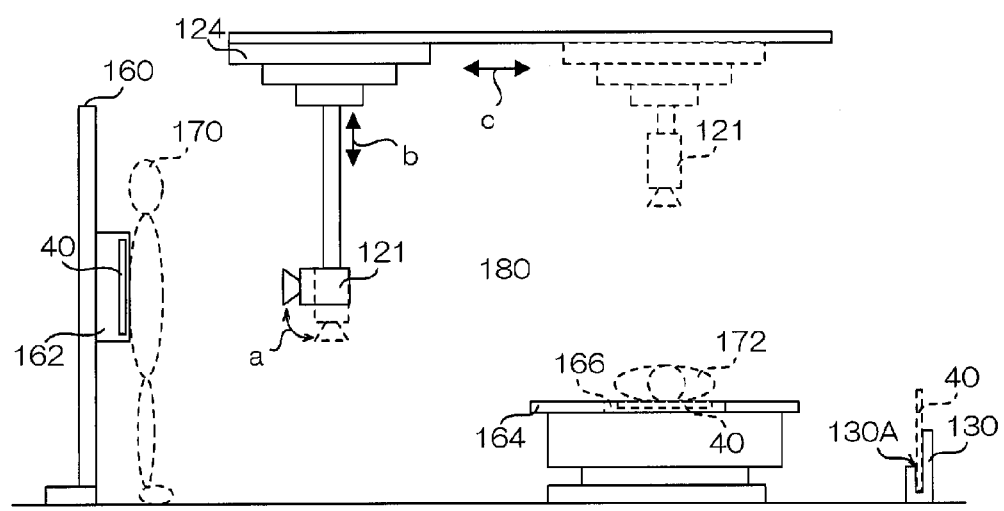
FIG. 2 is a side view illustrating an example arrangement of each device in a radiographic imaging room of a radiographic image capture system.

FIG. 2 shows an example arrangement of the devices in a radiographic imaging room 180 of the imaging system 104 pertaining to the present exemplary embodiment.

As shown in FIG. 2, a standing position stand 160, which is used in cases of performing radiographic imaging in a standing position, and a lying position table 164, which is used in cases of performing radiographic imaging in a lying position, are installed in the radiographic imaging room 180. The space in front of the standing position stand 160 serves as a subject imaging position 170 in cases of performing radiographic imaging in the standing position. The space above the lying position table 164 serves as a subject imaging position 172 in cases of performing radiographic imaging in the lying position.

A holding unit 162 that holds the electronic cassette 40 is disposed in the standing position stand 160. The electronic cassette 40 is held at the holding unit 162 in cases of capturing a radiographic image in the standing position. Similarly, a holding unit 166 that holds the electronic cassette 40 is disposed in the lying position table 164. The electronic cassette 40 is held at the holding unit 166 in cases of capturing a radiographic image in the lying position.

Further, a supporting and moving mechanism 124 is disposed in the radiographic imaging room 180. In order to enable both radiographic imaging in the standing position and in the lying position by radiation from the single radiation source 121, the supporting and moving mechanism 124 supports the radiation source 121 in such a way that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2). The supporting and moving mechanism 124 includes a drive source that rotates the radiation source 121 about the horizontal axis, a drive source that moves the radiation source 121 in the vertical direction, and a drive source that moves the radiation source 121 in the horizontal direction (illustration of the drive sources are omitted in the drawings).

An accommodating portion 130A that can accommodate the electronic cassette 40 is formed in the cradle 130.

When the electronic cassette 40 is not in use, the electronic cassette 40 is accommodated in the accommodating portion 130A of the cradle 130, and the built-in battery of the electronic cassette 40 is charged by the cradle 130. When a radiographic image is to be captured, the electronic cassette 40 is removed from the cradle 130 by, for example, a radiologic technologist and is held in the holding unit 162 of the standing position stand 160 if the imaging posture is the standing position, or is held in the holding unit 166 of the lying position table 164 if the imaging posture is the lying position.

In the imaging system 104 pertaining to the present exemplary embodiment, various types of information (data) are transmitted and received via wireless communication between the radiation generator 120 and the console 110 and between the electronic cassette 40 and the console 110.

The electronic cassette 40 is not limited to only being employed in a state held by the holding unit 162 of the standing position stand 160 or the holding unit 166 of the lying position table 164. Due to its portability, the electronic cassette 40 may also be employed unrestrained by a holding unit, for example in cases of imaging arm or leg regions of a subject.

Figure 3:
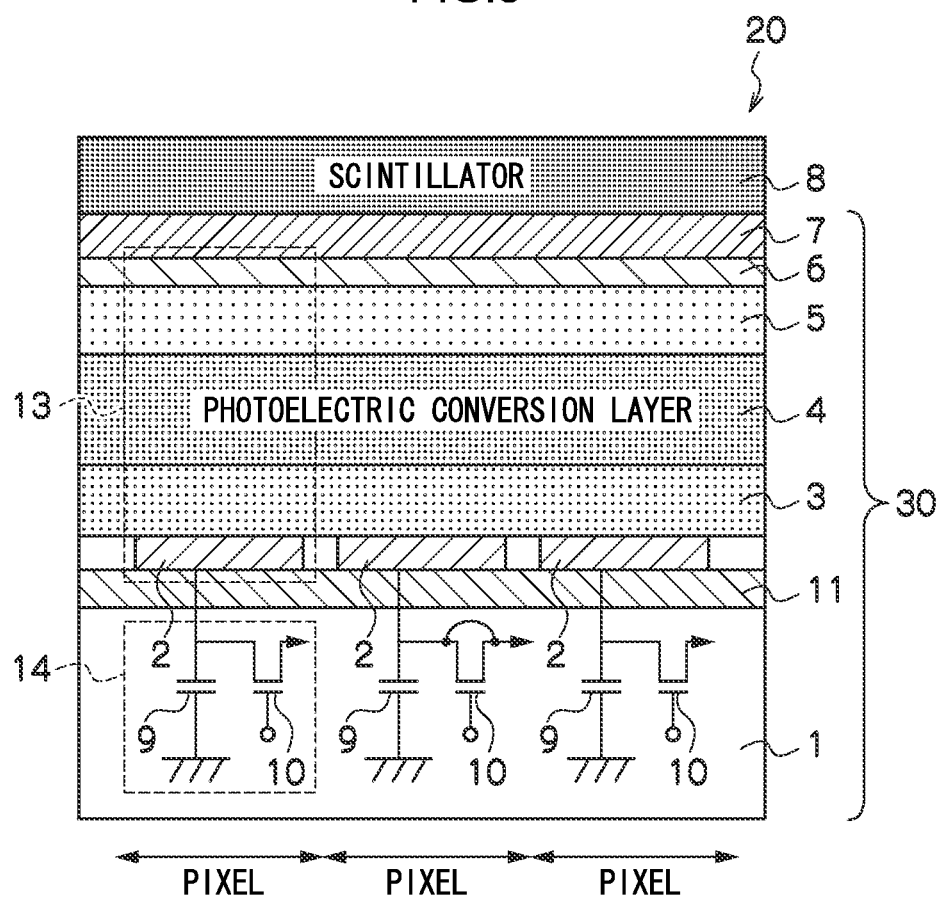
FIG. 3 is a cross-sectional diagram illustrating a schematic configuration of a portion including three pixels of a radiation detector of an exemplary embodiment.

Next, the configuration of the radiation detector 20 pertaining to the present exemplary embodiment will be described. FIG. 3 is a cross-sectional diagram schematically showing a portion including three pixels of the radiation detector 20.

As shown in FIG. 3, in the radiation detector 20 pertaining to the present exemplary embodiment, signal output portions 14, sensor portions 13, and a scintillator 8 are sequentially layered on an insulating substrate 1. Pixels are configured by the signal output portions 14 and the sensor portions 13. The pixels are arrayed on the substrate 1 and are configured such that the signal output portion 14 and the sensor portion 13 in each pixel have an overlap.

The scintillator 8 is formed on the sensor portions 13 with a transparent insulating film 7 being interposed therebetween. The scintillator 8 is formed as a film of a phosphor material that converts radiation made incident thereon from above (the opposite side of the substrate 1) or below into light and emits light. By providing the scintillator 8, the radiation that has passed through the subject is absorbed by the scintillator 8 and light is emitted.

It is preferred that the wavelength range of the light emitted by the scintillator 8 be in the visible light range (i.e., a wavelength of 360 nm to 830 nm). It is more preferred that the wavelength range of the light that the scintillator 8 emits include the green wavelength range in order to enable monochrome imaging by the radiation detector 20.

As the phosphor used for the scintillator 8, specifically a phosphor including cesium iodide (CsI) is preferred in cases of imaging using X-rays as radiation. Using CsI(Tl) (cesium iodide to which thallium has been added) whose emission spectrum when X-rays are applied is 400 nm to 700 nm is particularly preferred. The emission peak wavelength in the visible light range of CsI(Tl) is 565 nm.

The sensor portions 13 have an upper electrode 6, lower electrodes 2, and a photoelectric conversion layer 4 that is placed between the upper electrode 6 and the lower electrodes 2. The photoelectric conversion layer 4 is formed of an organic photoelectric conversion material that absorbs the light emitted by the scintillator 8 and generates electric charge.

It is preferred that the upper electrode 6 be formed of a conducting material that is transparent at least with respect to the emission wavelength of the scintillator 8, because it is necessary to allow the light produced by the scintillator 8 to be made incident on the photoelectric conversion layer 4. Specifically, using a transparent conducting oxide (TCO) whose transmittance with respect to visible light is high and whose resistance value is small is preferred. Although a metal thin film of Au or the like may also be used as the upper electrode 6, since its resistance value easily increases when trying to obtain a transmittance of 90% or more, TCO is more preferred. For example, ITO, IZO, AZO, FTO, $SnO_2$, $TiO_2$, $ZnO_2$ and the like may be preferably used. ITO is most preferred from the standpoints of process ease, low resistance, and transparency. The upper electrode 6 may have a single configuration common to all the pixels or may be divided per pixel.

The photoelectric conversion layer 4 includes an organic photoelectric conversion material, absorbs the light emitted from the scintillator 8, and generates an electric charge corresponding to the absorbed light. The photoelectric conversion layer 4 including the organic photoelectric conversion material has a sharp absorption spectrum in the visible range, and virtually no electromagnetic waves other than the light emitted by the scintillator 8 are absorbed by the photoelectric conversion layer 4. Therefore, noise that is generated as a result of radiation such as X-rays is effectively prevented from being absorbed by the photoelectric conversion layer 4.

It is preferred that the absorption peak wavelength of the organic photoelectric conversion material forming the photoelectric conversion layer 4 be as close as possible to the emission peak wavelength of the scintillator 8 so that the organic photoelectric conversion material most efficiently absorbs the light emitted by the scintillator 8. It is ideal that the absorption peak wavelength of the organic photoelectric conversion material and the emission peak wavelength of the scintillator 8 coincide, but as long as the difference between them is small, the organic photoelectric conversion material can sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm. It is more preferred that the difference be within 5 nm.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator 8, it is possible to make the difference between the peak wavelengths within 5 nm, and the amount of electric charge generated in the photoelectric conversion layer 4 may be substantially maximized.

Figure 4:
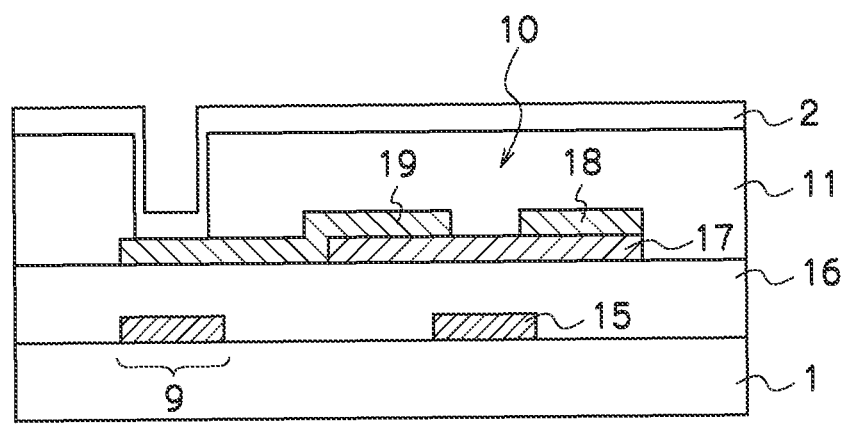
FIG. 4 a cross-sectional side view schematically illustrating the configuration of a signal output portion for a single pixel of the radiation detector.

The signal output portions 14 are formed on the surface of the substrate 1 below the lower electrodes 2 of the pixels. FIG. 4 schematically shows the configuration of one of the signal output portions 14.

As shown in FIG. 4, a capacitor 9 and a field-effect thin-film transistor (TFT) (hereinafter simply called as "thin-film transistor") 10 are formed in each of the signal output portions 14 in correspondence to the lower electrode 2. The capacitor 9 stores the electric charge that has moved to the lower electrode 2. The thin-film transistor 10 converts the electric charge stored in the capacitor 9 into an electric signal and outputs the electric signal. The region in which the capacitor 9 and the thin-film transistor 10 are formed has a portion that overlaps the lower electrode 2 in a plan view. Due to this configuration, the signal output portion 14 and the sensor portion 13 in each of the pixels have an overlap in the thickness direction. In order to minimize the plane area of the radiation detector 20 (the pixels), it is preferred that the region in which the capacitor 9 and the thin-film transistor 10 are formed be completely covered by the lower electrode 2.

The capacitor 9 is electrically connected to the corresponding lower electrode 2 via a wire of a conductive material penetrating an insulating film 11 that is disposed between the substrate 1 and the lower electrode 2. Because of this configuration, the electric charge trapped in the lower electrode 2 can be moved to the capacitor 9.

A gate electrode 15, a gate insulating film 16, and an active layer (channel layer) 17 are layered in the thin-film transistor 10. A source electrode 18 and a drain electrode 19 are formed a predetermined spacing apart from each other on the active layer 17.

The active layer 17 may, for example, be formed by amorphous silicon, an amorphous oxide, an organic semiconductor material, carbon nanotubes, or the like. However, the material configuring the active layer 17 is not limited to these.

In a case in which the active layer 17 is configured by an amorphous oxide, oxides including at least one of In, Ga, and Zn (e.g., In—O amorphous oxides) are preferred, oxides including at least two of In, Ga, and Zn (e.g., In—Zn—O amorphous oxides, In—Ga—O amorphous oxides, or Ga—Zn—O amorphous oxides) are more preferred, and oxides including all of In, Ga, and Zn are particularly preferred. As an In—Ga—Zn—O amorphous oxide, an amorphous oxide whose composition in a crystalline state is expressed by $InGaO_3(ZnO)_m$ (where m is a natural number less than 6) is preferred, and particularly $InGaZnO_4$ is preferred.

Examples of organic semiconductor materials capable of configuring the active layer 17 include phthalocyanine compounds, pentacene, and vanadyl phthalocyanine, but the organic semiconductor materials are not limited to these. Since configurations of phthalocyanine compounds are described in detail in JP-A No. 2009-212389, descriptions thereof will be omitted here.

The generation of noise in the signal output portion 14 may be effectively prevented in a case in which the active layer 17 of the thin-film transistor 10 is formed from an amorphous oxide, an organic semiconductor material, or carbon nanotubes, since such active layer 17 does not absorb radiation such as X-rays, or even if it does absorb any radiation, the absorbed radiation is an extremely minute amount.

In a case in which the active layer 17 is formed with carbon nanotubes, the switching speed of the thin-film transistor 10 is increased, and it is possible to form the thin-film transistor 10 having a low degree of absorption of light in the visible light range. In the case of forming the active layer 17 with carbon nanotubes, since the performance of the thin-film transistor 10 drops significantly even if an infinitesimal amount of a metal impurity is mixed into the active layer 17, it is necessary to separate, extract, and form extremely high-purity carbon nanotubes using centrifugal separation or the like.

Here, the amorphous oxide, organic semiconductor material, or carbon nanotubes that may configure the active layer 17 of the thin-film transistor 10 and the organic photoelectric conversion material forming the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a plastic or other flexible substrate, aramids, or bionanofibers may also be used. Specifically, substrates of polyester such as polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) or other flexible substrates may be used. By employing a flexible substrate made of plastic, the substrate may be made lightweight, which is advantageous for portability.

Further, an insulating layer for ensuring insulation, a gas barrier layer for preventing the transmission of moisture and/or oxygen, an undercoat layer for improving flatness or adhesion to the electrodes or the like, or other layers may also be disposed on the substrate 1.

Meantime, since high-temperature processes of 200 degrees or higher can be applied to aramids, a transparent electrode material can be hardened at a high temperature and given a low resistance. Aramids can also accommodate automatic packaging of driver ICs including solder reflow processes. Aramids also have a thermal expansion coefficient that is close to that of indium tin oxide (ITO) or a glass substrate, so they have little warping after manufacture and do not break easily. Further, it is possible to form the substrate 1 thinner with aramids compared to a glass substrate or the like. An ultrathin glass substrate and an aramid may also be layered to form a substrate.

Bionanofibers are composites of cellulose microfibril bundles (bacterial cellulose) that a bacterium (*Acetobacter xylinum*) produces and a transparent resin. Cellulose microfibril bundles have a width of 50 nm, which is a size that is 1/10 with respect to visible wavelengths, and have high strength, high elasticity, and low thermal expansion. By impregnating and hardening a transparent resin such as an acrylic resin or an epoxy resin in bacterial cellulose, it is possible to obtain bionanofibers exhibiting a light transmittance of about 90% at a wavelength of 500 nm while including fibers at 60 to 70%. Since bionanofibers have a low thermal expansion coefficient (3 to 7 ppm) comparable to silicon crystal, a strength comparable to steel (460 MPa), high elasticity (30 GPa), and are flexible, they enable to form the substrate 1 thinner compared to a glass substrate or the like.

In the present exemplary embodiment, a TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
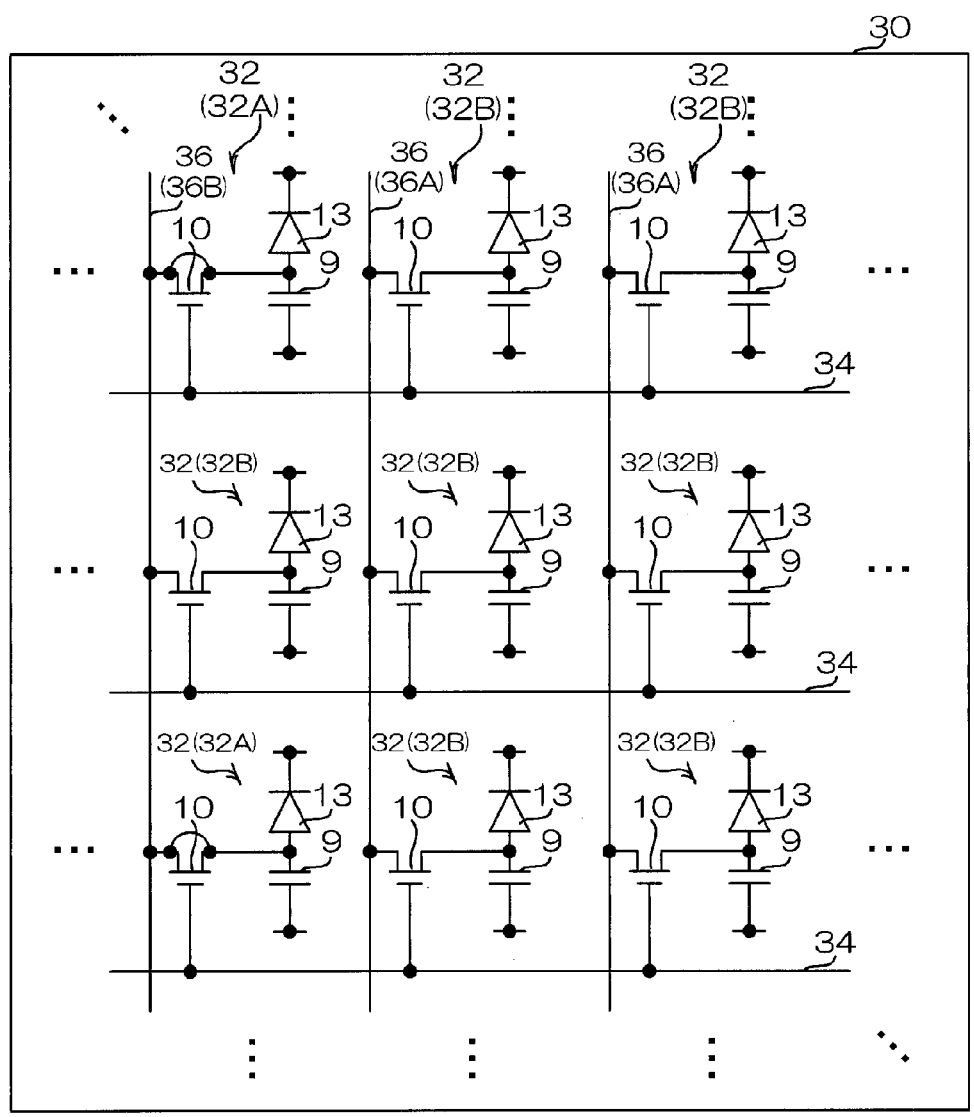
FIG. 5 is a plan view illustrating the configuration of the radiation detector.

As illustrated in FIG. 5, on the TFT substrate 30, plural pixels 32 including the sensor portions 13, the capacitors 9, and the thin-film transistors 10 are disposed two-dimensionally in one direction (a direction along gate lines 34 in FIG. 5) and an intersecting direction (a direction along signal lines 36 in FIG. 5) with respect to the one direction.

Further, plural gate lines 34 that extends in the one direction and are for switching ON and OFF the thin-film transistors 10 and plural signal lines 36 that extends in the intersecting direction and are for reading out the electric charges via the thin-film transistors 10 that is switched ON, are disposed in the radiation detector 20.

The radiation detector 20 is formed in a tabular, quadrilateral shape having four sides on its outer edges in a plan view. More specifically, the radiation detector 20 is formed in a rectangular shape.

In the radiation detector 20 pertaining to the present exemplary embodiment, some of the pixels 32 are used for detecting irradiation of radiation, and the remaining pixels 32 are used for capturing radiographic images. Hereinafter, the pixels 32 for detecting irradiation of radiation will be called radiation detection pixels (detection pixels) 32A, and the remaining pixels 32 will be called radiographic imaging pixels (imaging pixels) 32B.

As illustrated in FIG. 5, the detection pixels 32A according to the present exemplary embodiment are configured with thin-film transistors 10 that are each shorted across the source and drain. Therefore, in the detection pixels 32A, the electric charge that has been accumulated in each of the capacitors 9 flows out to the signal lines 36 irrespective of the switching state of the thin-film transistors 10.

The radiation detector 20 cannot obtain pixel information (data) of radiographic images in the positions where the radiation detection pixels 32A are placed because the radiation detector 20 captures radiographic images with the imaging pixels 32B excluding the detection pixels 32A of the pixels 32. For this reason, in the radiation detector 20, the detection pixels 32A are placed so as to be dispersed, and the console 110 executes missing pixel correction that generates pixel data of radiographic images in the positions where the detection pixels 32A are placed by interpolation using pixel data that has been obtained by the imaging pixels 32B positioned around those detection pixels 32A.

Figure 6:
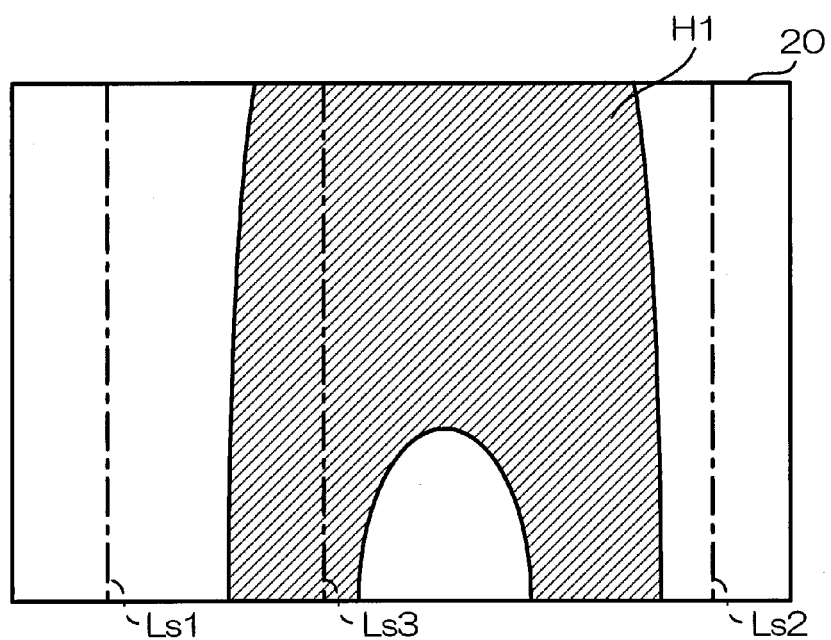
FIG. 6 is another plan view illustrating the configuration of the radiation detector.

As illustrated in the example of FIG. 6, the radiation detector 20 according to the present exemplary embodiment is configured such that the detection pixels 32A and the imaging pixels 32B are arrayed in plural lines, in which some of the plural lines (three in the present exemplary embodiment) Ls1, Ls2, Ls3, which are referred to below as "detection pixel lines", include both detection pixels 32A and imaging pixels 32B.

In the radiation detector 20, as illustrated in the example of FIG. 6, the detection pixel lines Ls1, Ls2, Ls3 are disposed at three locations, which are a region at a central portion of the imaging region of the radiation detector 20 where there is a high possibility to be a subject positioned region H1, and regions at each of the two sides of the imaging region of the radiation detector 20 where there is a high possibility that the subject is not positioned. Further, in the radiation detector 20, the number of detection pixels 32A included in each of the detection pixel lines is a constant number (20 in the present exemplary embodiment).

Figure 7:
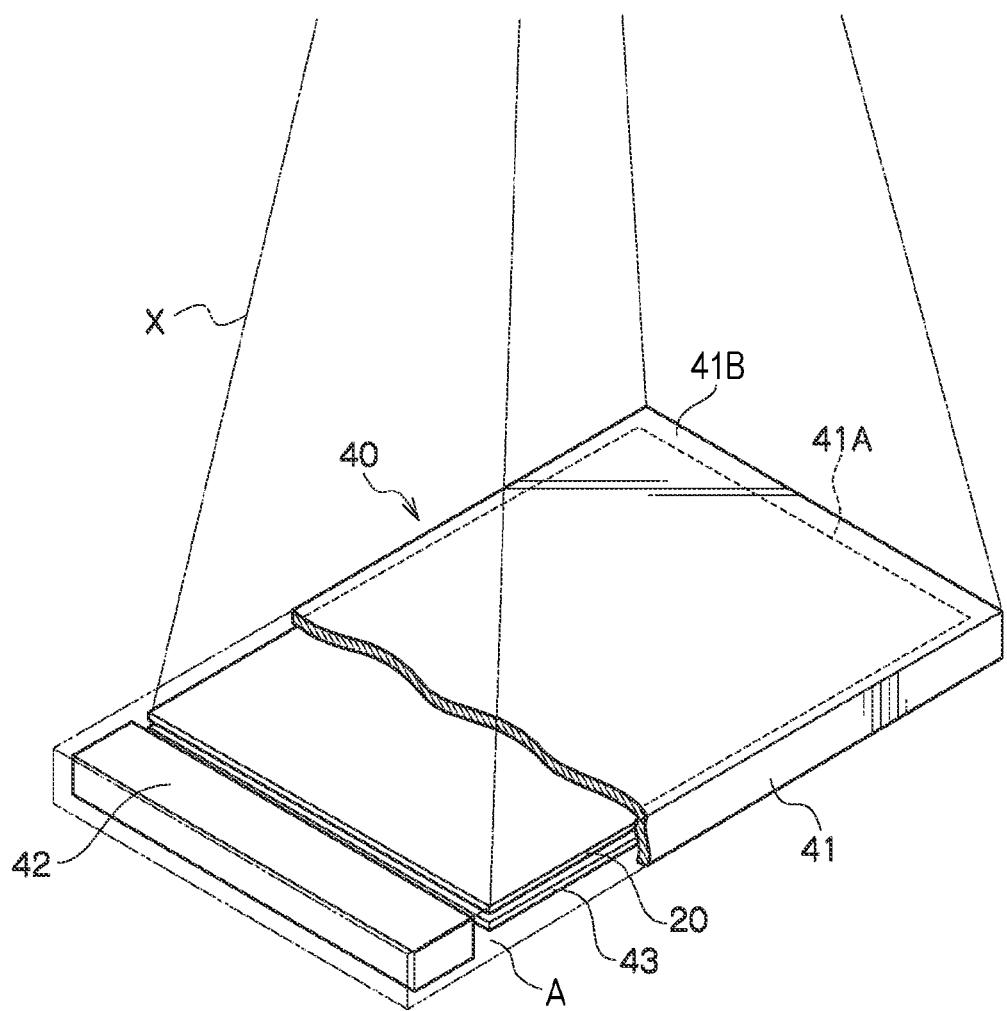
FIG. 7 is a perspective view illustrating the configuration of an electronic cassette of an exemplary embodiment.

Next, the configuration of the electronic cassette 40 pertaining to the present exemplary embodiment will be described. FIG. 7 is a perspective view illustrating the configuration of the electronic cassette 40.

As shown in FIG. 7, the electronic cassette 40 is equipped with a housing 41 that is formed from a material that allows radiation to pass through, and the electronic cassette 40 is given a waterproof and airtight structure. In a case in which the electronic cassette 40 is used in an operating room or the like, there is the concern that blood or other contaminants may adhere to the electronic cassette 40. Therefore, by giving the electronic cassette 40 a waterproof and airtight structure and disinfecting the electronic cassette 40 as needed, the single electronic cassette 40 may be used repeatedly.

A space A that accommodates various parts is formed inside the housing 41. The radiation detector 20 that detects the radiation X that has passed through the subject, and a lead plate 43 that absorbs backscattered rays of the radiation X, are disposed in this order inside the space A from a side of the housing 41 on which the radiation X is irradiated.

In the electronic cassette 40, the region in one surface of the tabular shape of the housing 41, which corresponds to the position at which the radiation detector 20 is disposed, is configured as a quadrilateral imaging region 41A that is capable of detecting radiation. The surface having the imaging region 41A of the housing 41 serves as a top plate 41B of the electronic cassette 40. In the electronic cassette 40, the radiation detector 20 is placed such that the TFT substrate 30 is disposed at the top plate 41B side, and the radiation detector 20 is adhered to the inner surface of the top plate 41B (the back surface of the top plate 41B at the opposite side of the surface on which the radiation is made incident) of the housing 41.

As shown in FIG. 7, a case 42 that accommodates a cassette controller 58 and a power supply section 70 (see also FIG. 9) is placed at one end side of the interior of the housing 41 in a position that does not overlap with the radiation detector 20 (i.e., outside the range of the imaging region 41A).

The housing 41 is formed of carbon fiber, aluminum, magnesium, bionanofibers (cellulose microfibrils) or a composite material, for example, in order to make the entire electronic cassette 40 lightweight.

As the composite material, for example, a material including reinforced fiber resin is used, and carbon, cellulose or the like is included in the reinforced fiber resin. Specifically, carbon fiber reinforced plastic (CFRP), a composite material with a structure in which a foam material is sandwiched by CFRP, or a composite material in which the surface of a foam material is coated with CFRP may be used as the composite material. In the present exemplary embodiment, a composite material with a structure in which a foam material is sandwiched by CFRP is used. Thereby, the strength (rigidity) of the housing 41 may be raised compared to a case in which the housing 41 is configured only by a carbon.

Figure 8:
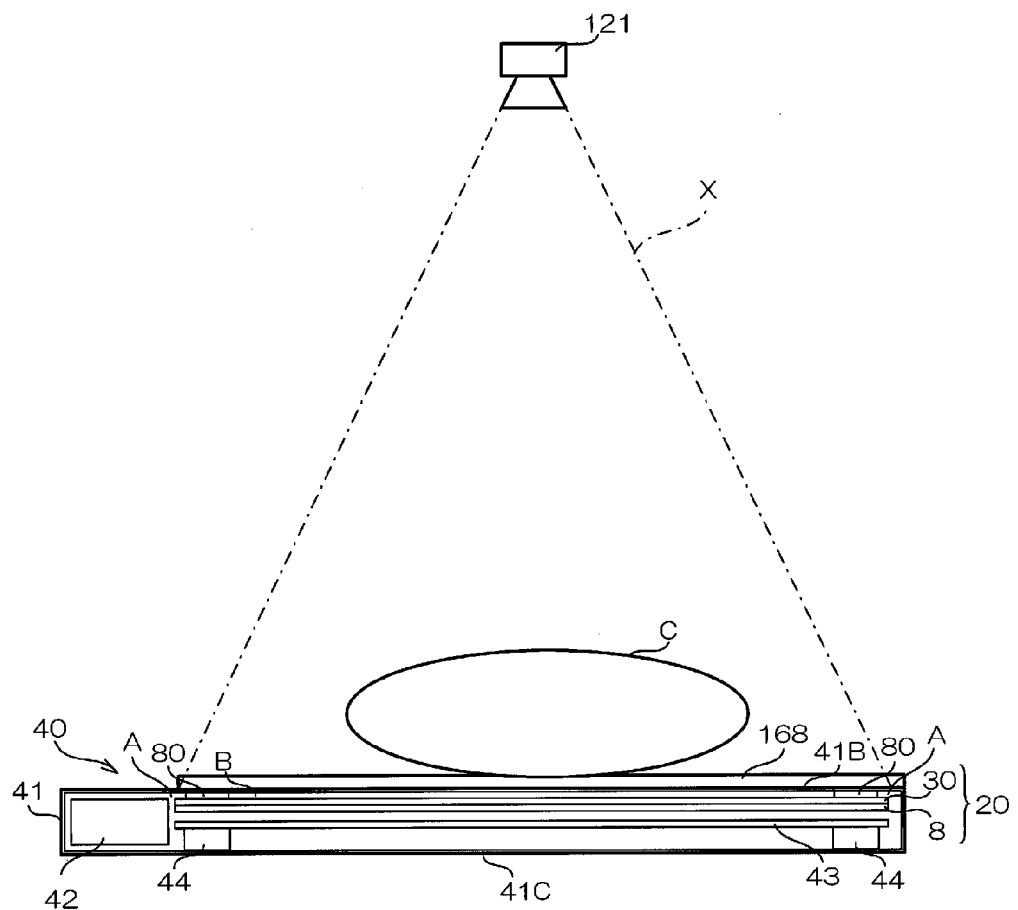
FIG. 8 is a cross-sectional side view illustrating the electronic cassette.

As shown in FIG. 8, inside the housing 41, support members 44 are disposed on the inner surface of a back surface 41C opposing the top plate 41B. The radiation detector 20 and the lead plate 43 are placed in this order in the irradiation direction of the radiation X between the support members 44 and the top plate 41B. The support members 44 that support the lead plate 43 are formed of a foam material, for example, from the standpoint of reducing weight and absorbing dimensional deviations.

As shown in FIG. 8, adhesive members 80 that detachably adhere the TFT substrate 30 of the radiation detector 20 to the top plate 41B are disposed at the inner surface of the top plate 41B. Double-sided tape, for example, may be used as the adhesive members 80. In this case, the double-sided tape 80 is formed such that the adhesive force of one adhesive surface is stronger than that of the other adhesive surface.

Specifically, the surface having a weak adhesive force (weak adhesive surface) is set to have a 180-degree peel strength equal to or less than 1.0 N/cm. The surface having a strong adhesive force (strong adhesive surface) contacts the top plate 41B, and the weak adhesive surface contacts the TFT substrate 30. Because of this configuration, the thickness of the electronic cassette 40 may be made thin compared to a case in which the radiation detector 20 is fixed to the top plate 41B by, for example, fixing members such as screws. Further, even if the top plate 41B deforms due to a shock or a load, the radiation detector 20 follows the deformation of the top plate 41B, which has high rigidity. Therefore, only deformation of large curvature (a gentle curve) arises in the radiation detector 20 and the potential for the radiation detector 20 to break due to localized deformation of low curvature can be reduced. Moreover, the radiation detector 20 may contribute to improving the rigidity of the top plate 41B.

In this way, since the radiation detector 20 is adhered to the inner surface of the top plate 41B of the housing 41 of the electronic cassette 40, the housing 41 is separable into two between the top plate 41B side and the back surface 41C side. The housing 41 may be separated into two of the top plate 41B side and the back surface 41C side when the radiation detector 20 is adhered to the top plate 41B or when the radiation detector 20 is detached from the top plate 41B.

In the present exemplary embodiment, the adhesion of the radiation detector 20 to the top plate 41B does not have to be performed in a clean room or the like. The reason is because, even if foreign materials such as metal fragments that absorb radiation have been incorporated between the radiation detector 20 and the top plate 41B, the foreign materials can be removed by detaching the radiation detector 20 from the top plate 41B.

Next, the configurations of relevant portions of an electrical system of the imaging system 104 pertaining to the present exemplary embodiment will be described with reference to FIG. 9.

Figure 9:
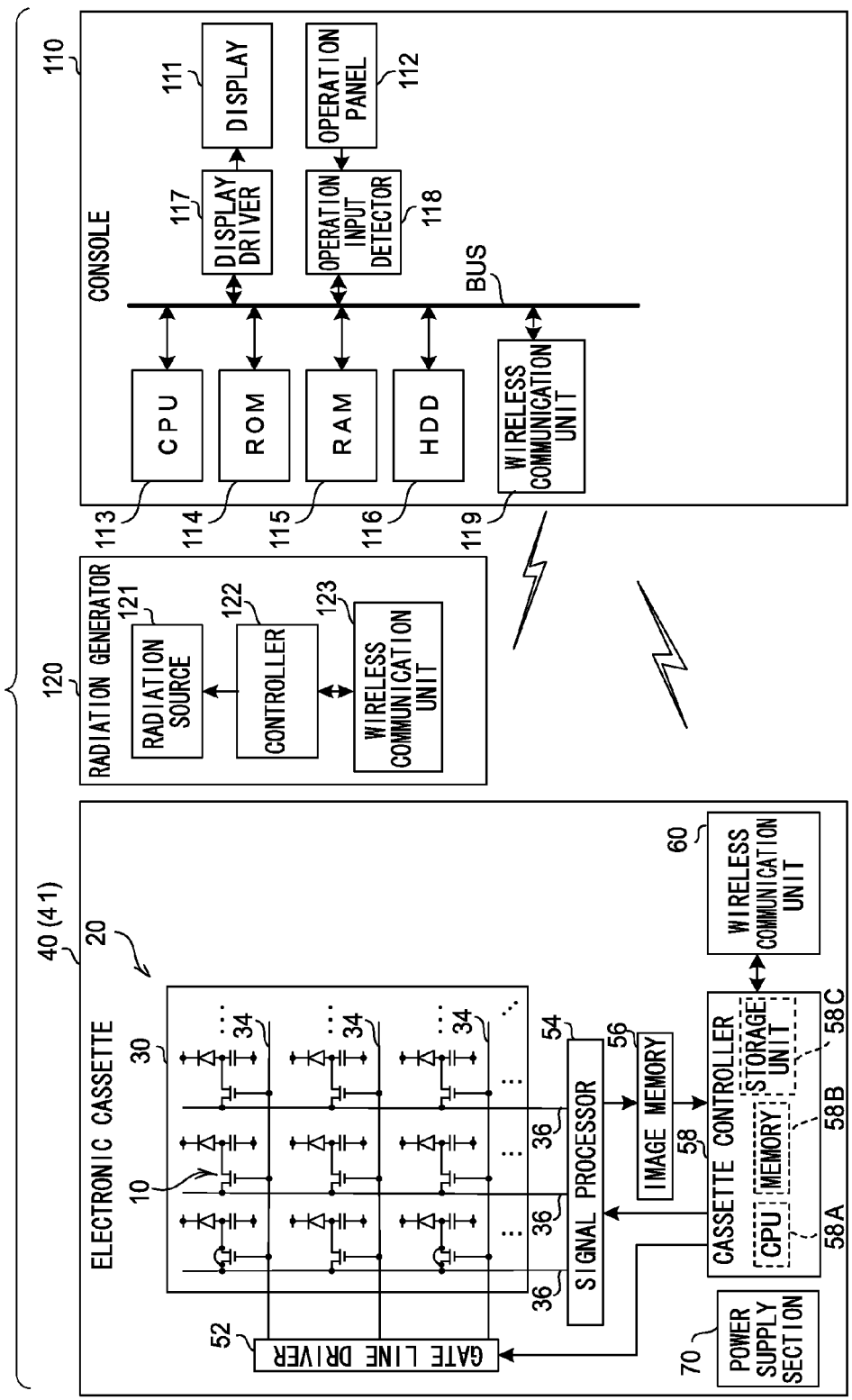
FIG. 9 is a block diagram illustrating relevant portions of an electrical system of the radiographic image capture system.

As shown in FIG. 9, in the radiation detector 20 built into the electronic cassette 40, a gate line driver 52 is placed on one side of two sides adjacent to each other, and a signal processor 54 is placed on the other side. The individual gate lines 34 of the TFT substrate 30 are connected to the gate line driver 52, and the individual signal lines 36 of the TFT substrate 30 are connected to the signal processor 54.

An image memory 56, the cassette controller 58, and a wireless communication unit 60 are disposed inside the housing 41.

The thin-film transistors 10 of the TFT substrate 30 are sequentially switched on in row units (i.e., per gate line 34) by signals supplied via the gate lines 34 from the gate line driver 52. The electric charges that have been read out by the thin-film transistors 10 that has been switched ON are transmitted through the signal lines 36 as electric signals and are inputted to the signal processor 54. Thus, the electric charges are sequentially read out per gate line 34, and a two-dimensional radiographic image is acquired.

While omitted from illustration, for every signal line 36, the signal processor 54 is equipped with an amplifier circuit for amplifying input electrical signals, and a sample-and-hold circuit. Electric signals transmitted by the signal lines 36 are held in the sample-and-hold circuits after amplification by the amplifier circuits. A multiplexer and an analog-to-digital (A/D) converter are connected in sequence to the output side of the sample-and-hold circuits. The electric signals held in the respective sample-and-hold circuits are input in sequence (serially) to the multiplexer and converted into digital image data by the A/D converter.

The image memory 56 is connected to the signal processor 54. The image data output from the A/D converter of the signal processor 54 are sequentially stored in the image memory 56. The image memory 56 has a storage capacity that is capable of storing image data for a predetermined number of frames' worth of radiographic images. Each time radiographic imaging is performed, the image data obtained by the imaging are sequentially stored in the image memory 56.

The image memory 56 is also connected to the cassette controller 58. The cassette controller 58 includes a microcomputer that is equipped with a central processing unit (CPU) 58A, a memory 58B including a read-only memory (ROM) and a random access memory (RAM), and a nonvolatile storage unit 58C including a flash memory or the like, and controls the operations of the entire electronic cassette 40.

The wireless communication unit 60 is connected to the cassette controller 58. The wireless communication unit 60 is adapted to a wireless local area network (LAN) standard represented by IEEE (Institute of Electrical and Electronics Engineers) 802.11a/b/g/n or the like and controls the transmission of various types of information (data) between the electronic cassette 40 and external devices by wireless communication. Via the wireless communication unit 60, the cassette controller 58 is made capable of wireless communication with external devices such as the console 110 that performs control relating to radiographic imaging, and is made capable of transmitting and receiving various types of data to and from the console 110 and the like.

Further, the power supply section 70 is disposed in the electronic cassette 40. The various circuits and elements described above (the gate line driver 52, the signal processor 54, the image memory 56, the wireless communication unit 60, the microcomputer functioning as the cassette controller 58, etc.) are actuated by power supplied from the power supply section 70. The power supply section 70 has a built-in battery (a rechargeable secondary battery) so as to not impair the portability of the electronic cassette 40, and the power supply section 70 supplies power to the various circuits and elements from the charged battery. In FIG. 9, illustration of wires connecting the various circuits and elements to the power supply section 70 is omitted.

As shown in FIG. 9, the console 110 is configured as a server computer and is equipped with a display 111 that displays operation menus, captured radiographic images and so forth, and an operation panel 112 that is configured to include plural keys and by which various types of information (data) and operation instructions are input.

The console 110 is equipped with a CPU 113 that controls the operations of the entire device, a ROM 114 in which various programs including a control program are stored in advance, a RAM 115 that temporarily stores various types of data, a hard disk drive (HDD) 116 that stores and holds various types of data, a display driver 117 that controls the display of various types of information on the display 111, and an operation input detector 118 that detects states of operation with respect to the operation panel 112. Further, the console 110 is equipped with a wireless communication unit 119 that transmits and receives various types of information (data) such as later-described exposure conditions to and from the radiation generator 120 by wireless communication, and also transmits and receives various types of information (data) such as image data to and from the electronic cassette 40 by wireless communication.

The CPU 113, the ROM 114, the RAM 115, the HDD 116, the display driver 117, the operation input detector 118, and the wireless communication unit 119 are connected to each other via a system bus BUS. Consequently, the CPU 113 is capable to access the ROM 114, the RAM 115, and the HDD 116, to control the display of various types of information on the display 111 via the display driver 117, and to control the transmission and reception of various types of information (data) to and from the radiation generator 120 and the electronic cassette 40 via the wireless communication unit 119. Further, the CPU 113 is capable to grasp states of operation by a user with respect to the operation panel 112 via the operation input detector 118.

The radiation generator 120 is equipped with the radiation source 121, a wireless communication unit 123 that transmits and receives various types of information (data) such as the exposure conditions to and from the console 110, and a controller 122 that controls the radiation source 121 based on the received exposure conditions.

The controller 122 also includes a microcomputer and stores the received exposure conditions and so forth. The exposure conditions received from the console 110 include information such as tube voltage, tube current and the like. The controller 122 causes the radiation source 121 to emit the radiation X based on the received exposure conditions.

The electronic cassette 40 according to the present exemplary embodiment has a radiation determination function that determines whether or not radiation has been detected by electronic cassette 40 based on the values obtained by the detection pixel lines Ls1, Ls2, Ls3 of the radiation detector 20.

Explanation follows regarding the radiation determination function according to the present exemplary embodiment.

The inventors have performed the following tests in order to confirm the influence on values (referred to below as "radiation detection determination values") representing the electric charges that have been read from the signal lines 36 corresponding to the detection pixel lines Ls1, Ls2, Ls3 (referred to below as signal lines 36B) arising when a shock is imparted and when extraneous noise from an electromagnetic field is added to the electronic cassette 40.

Namely, sampling of the radiation detection determination value is performed successively a plural number of times in a case in which a shock is imparted to the electronic cassette 40 (referred to below as a first condition), in a case in which extraneous noise is applied to the electronic cassette 40 (referred to below as a second condition), and in a case in which radiation is irradiated onto the electronic cassette 40 without a shock or extraneous noise is being applied to the electronic cassette 40 (referred to below as a third condition).

Figure 10:
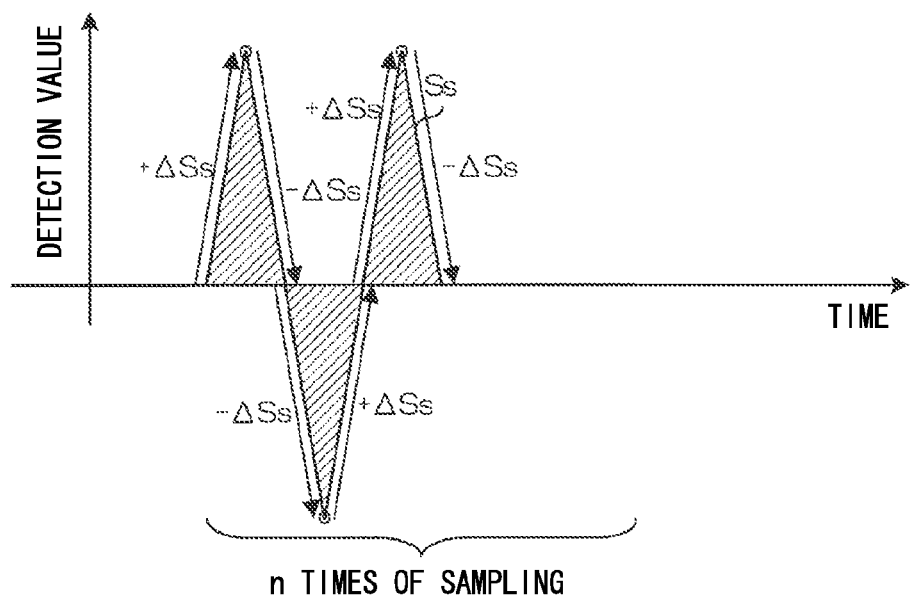
FIG. 10 is a graph illustrating an example of a relationship between elapsed time and detection values to explain a radiation determination function according to an exemplary embodiment.
Figure 11:
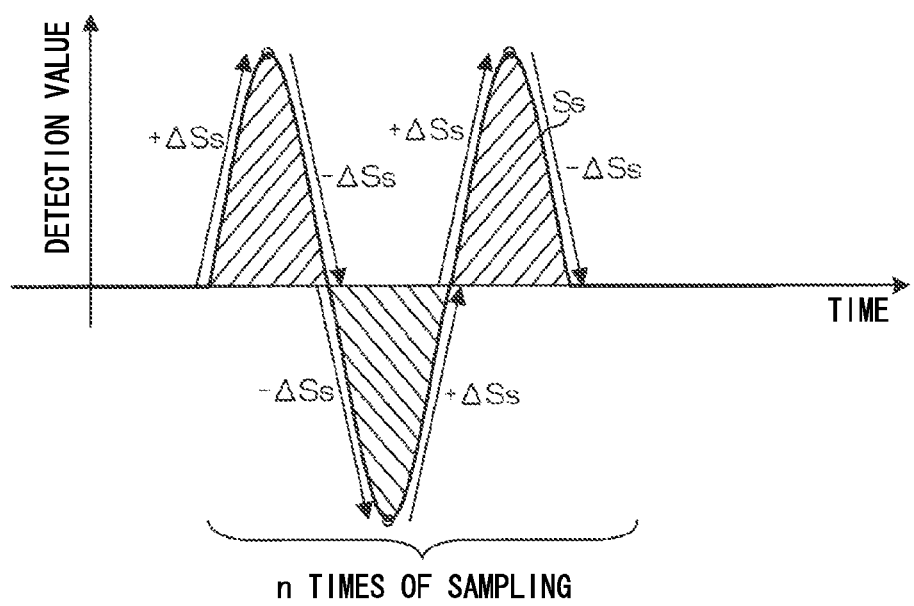
FIG. 11 is a graph illustrating an example of a relationship between elapsed time and detection values to explain the radiation determination function.
Figure 12:
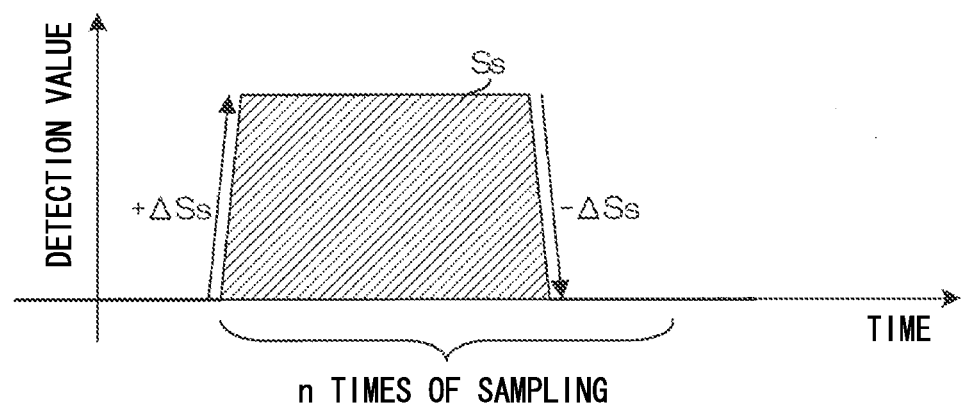
FIG. 12 is a graph illustrating an example of a relationship between elapsed time and detection values to explain the radiation determination function.
Figure 13:
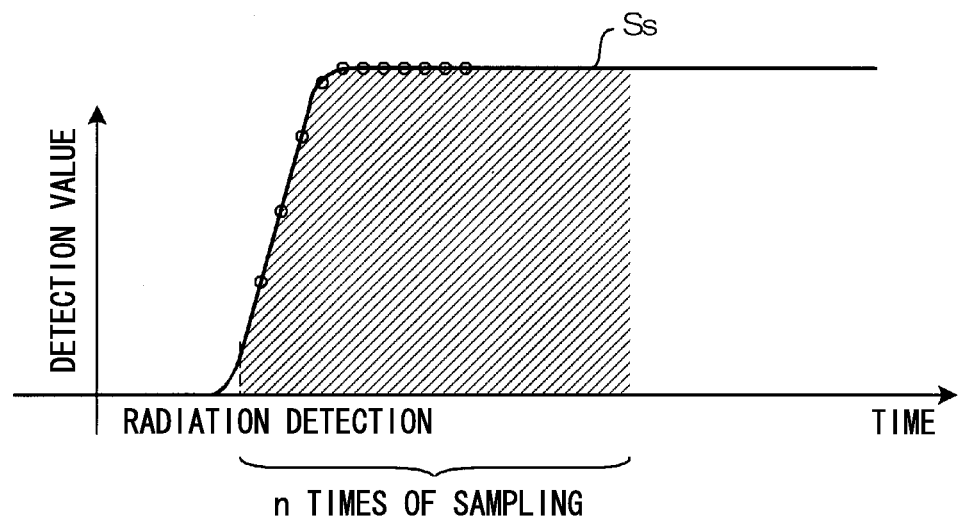
FIG. 13 is a graph illustrating an example of a relationship between elapsed time and detection values to explain the radiation determination function.

FIG. 10 illustrates an example of changes with time in the radiation detection determination value Ss obtained under the first condition. FIG. 11 illustrates an example of changes with time in the radiation detection determination value Ss obtained under the second condition. FIG. 12 and FIG. 13 illustrate examples of changes with time in the radiation detection determination value Ss obtained under the third condition. Note that FIG. 12 gives an example of a case wherein the radiation irradiation duration is shorter than the sampling duration, and FIG. 13 gives an example of a case wherein the radiation irradiation duration is longer than the sampling duration.

As is clear from these diagrams, the radiation detection determination values Ss obtained under the first condition and the second condition fluctuate so as to oscillate with a comparatively large amplitude. In contrast, no such oscillation occurs in the radiation detection determination value Ss obtained under the third condition.

The radiation determination function according to the present exemplary embodiment employs an integration value of radiation detection determination value Ss over a predetermined period of time (referred to below as the first integration value) and an integration value of change amounts ΔSs per specific time duration of the radiation detection determination value Ss over the predetermined period of time (referred to below as the second integration value) for determination as to whether or not radiation has been detected. Thereby, the present exemplary embodiment enables radiation detection at high precision.

Further, the radiation determination function according to the present exemplary embodiment employs a ratio of the first integration value and the second integration value in determination as to whether or not radiation has been detected. Accordingly radiation detection can be performed at high precision irrespective of the irradiation amount of radiation in comparison to cases in which the difference between the first integration value and the second integration value is employed for radiation detection.

The radiation determination function employs the radiation detection determination value Ss that has been successively sampled n times, and ultimately derives a first integration value S1 and a second integration value S2 by computing values obtained according to the following Equation (1) and Equation (2). The modulus portion in the right side of Equation (2) corresponds to the change amount ΔSs.

$$S1 = \sum_{i=1}^{n} Ss_i \quad (1)$$

$$S2 = \sum_{i=2}^{n} |Ss_i - Ss_{i-1}| \quad (2)$$

Then, in the radiation determination function, a ratio R is derived according to the following Equation (3), and determination is made that radiation has been detected if the ratio R is equal to or greater than a predetermined threshold value, and otherwise, determination is made that radiation has not been detected.

$$R = \frac{S2}{S1} \quad (3)$$

Explanation follows regarding operation of the imaging system 104 according to the present exemplary embodiment.

Figure 14:
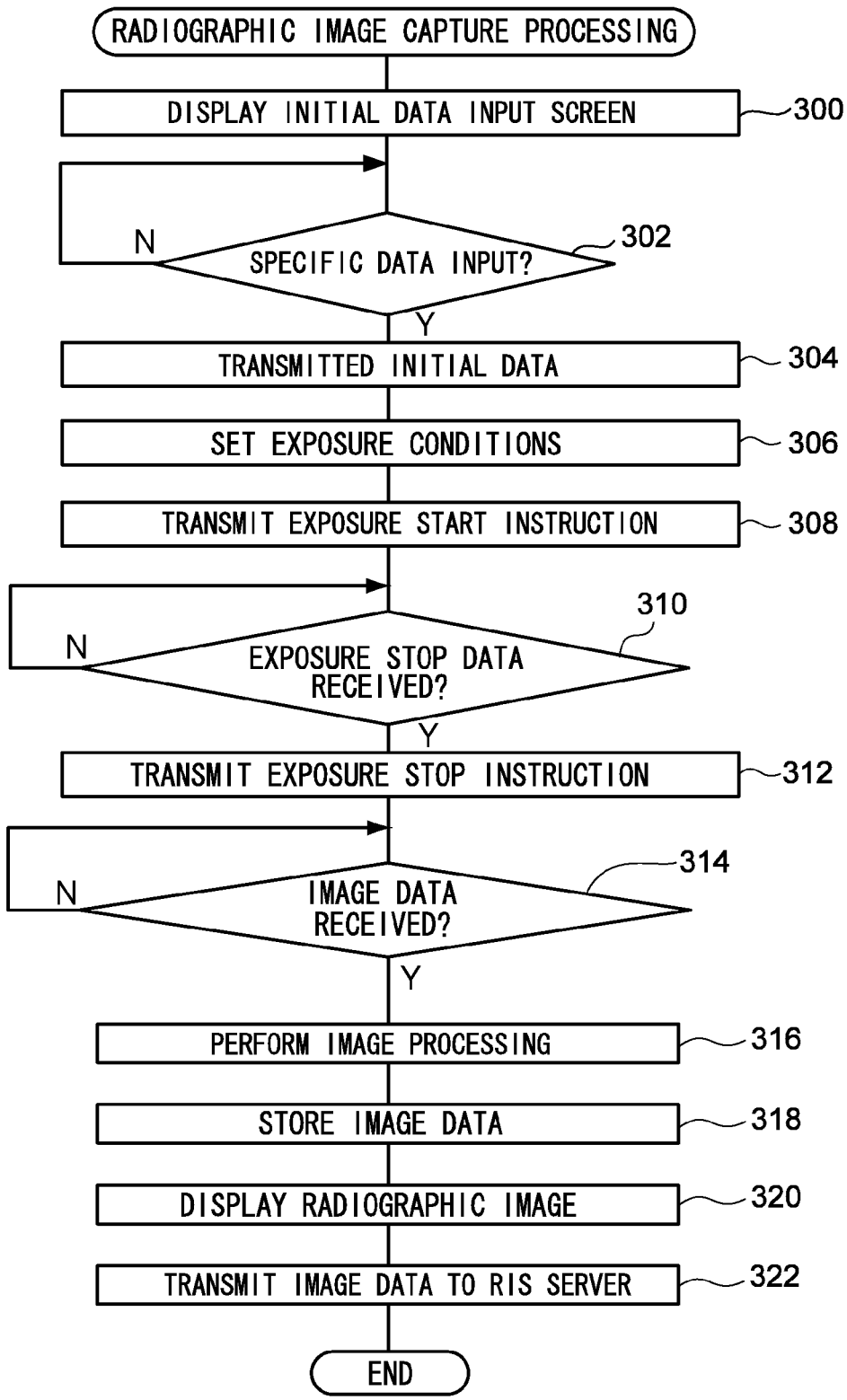
FIG. 14 is a flow chart illustrating the flow of processing of a radiographic image capture program according to an exemplary embodiment.

First, explanation follows regarding operation of the console 110 in a case of capturing a radiographic image, with reference to FIG. 14. FIG. 14 is a flow chart illustrating a flow of processing in a radiographic image capture processing program executed by the CPU 113 of the console 110 after an execution instruction has been input via the operation panel 112. The program is installed in a specific region of the ROM 114.

At step 300 of FIG. 14, the console 110 causes the display driver 117 to display an initial data input screen on the display 111, and then stands by at the next step 302 for specific data input.

FIG. 15 illustrates an example of the initial data input screen displayed on the display 111 by the processing of step 300. As illustrated in FIG. 15, the initial data input screen according to the present exemplary embodiment displays a message to prompt input of the name of a subject for radiographic image capture, imaging target site, posture during imaging, and radiation X exposure conditions during imaging (tube voltage and tube current during radiation X exposure in the present exemplary embodiment), and displays input fields for such data.

After the initial data input screen illustrated in FIG. 15 has been displayed by the display 111, the imaging technician may input the name of the subject for image capture, the imaging target site, the posture for image capture and the exposure conditions to each corresponding input field using the operation panel 112.

Then the imaging technician may enter the radiographic imaging room 180 together with the subject, and after first retaining the electronic cassette 40 on the holding unit 162 of the standing position stand 160 or the holding unit 166 of the lying position table 164, corresponding respectively to standing or lying posture during imaging, and positioning the radiation source 121 in a corresponding position, the imaging technician may position the subject in a specific imaging position. If a radiographic image for an imaging target site such as an arm region or leg region is to be captured with the electronic cassette 40 not retained by a holding unit, the imaging technician may position the subject, the electronic cassette 40 and the radiation source 121 in a state in which image capture of the imaging target site is possible.

Then, the imaging technician may leave the radiographic imaging room 180 and select a complete button displayed in the vicinity of the bottom edge of the initial data input screen using the operation panel 112. If the complete button is selected by the imaging technician, affirmative determination is made at step 302, and processing transitions to step 304.

At step 304, the console 110 transmits the data that has been input in the initial data input screen, which is referred to below as initial data, to the electronic cassette 40 using the wireless communication unit 119. Then at the next step 306, the exposure conditions contained in the initial data are transmitted to the radiation generator 120 using the wireless communication unit 119 to set the exposure conditions. In response, the controller 122 of the radiation generator 120 performs exposure preparation based on the received exposure conditions.

At the next step 308, the console 110 transmits instruction data instructing initiation of exposure to the radiation generator 120 and the electronic cassette 40 using the wireless communication unit 119.

In response, the radiation source 121 starts emitting the radiation X with the tube voltage and tube current corresponding to the exposure conditions that the radiation generator 120 received from the console 110. The radiation X emitted from the radiation source 121 arrives at the electronic cassette 40 after passing through the subject.

Meanwhile, on receipt of the instruction data instructing initiation of exposure, the cassette controller 58 of the electronic cassette 40 switches ON the thin-film transistors 10 of all the radiation detector 20, and stands by until a radiation amount obtained based on image data stored in the image memory 56 according to the electric charges read from each of the signal lines 36 (referred to below as "radiation detection image data") reaches or exceeds a predetermined threshold value used for detecting that radiation irradiation has started. The electronic cassette 40 then determines whether or not the detection value indicates actual irradiation of radiation using the radiation determination function. Only if it is determined that radiation has been detected, the electronic cassette 40 performs radiographic image capture operation, and then transmits exposure stop data instructing termination of irradiation of radiation X to the console 110.

The console 110 stands by at the next step 310 for receipt of the exposure stop data. At the next step 312, the console 110 transmits instruction data instructing termination of irradiation of radiation X to the radiation generator 120 using the wireless communication unit 119. In response, irradiation of radiation X from the radiation source 121 is stopped.

After the radiographic image capture operation is completed, the electronic cassette 40 transmits the image data obtained by image capture to the console 110.

The console 110 stands by at the next step 314 for receipt of the image data from the electronic cassette 40, and at the next step 316 the console 110 subjects the received image data to the previously mentioned missing pixel correction processing, and then executes image processing to perform various types of correction, such as shading correction.

At the next step 318, the console 110 stores the image data to which the above image processing has been performed (referred to below as "corrected image data") in the HDD 116. Then at the next step 320, the console 110 causes the display driver 117 to display a radiographic image expressed by the corrected image data on the display 111 in order to perform verification or other operation.

At the next step 322, the console 110 transmits the corrected image data to the RIS server 150 via the in-hospital network 102, and then ends the radiographic image capture processing program. The corrected image data transmitted to the RIS server 150 is stored in the database 150A, enabling a doctor to perform, for example, interpretation of the captured radiographic image and diagnosis.

Figure 16:
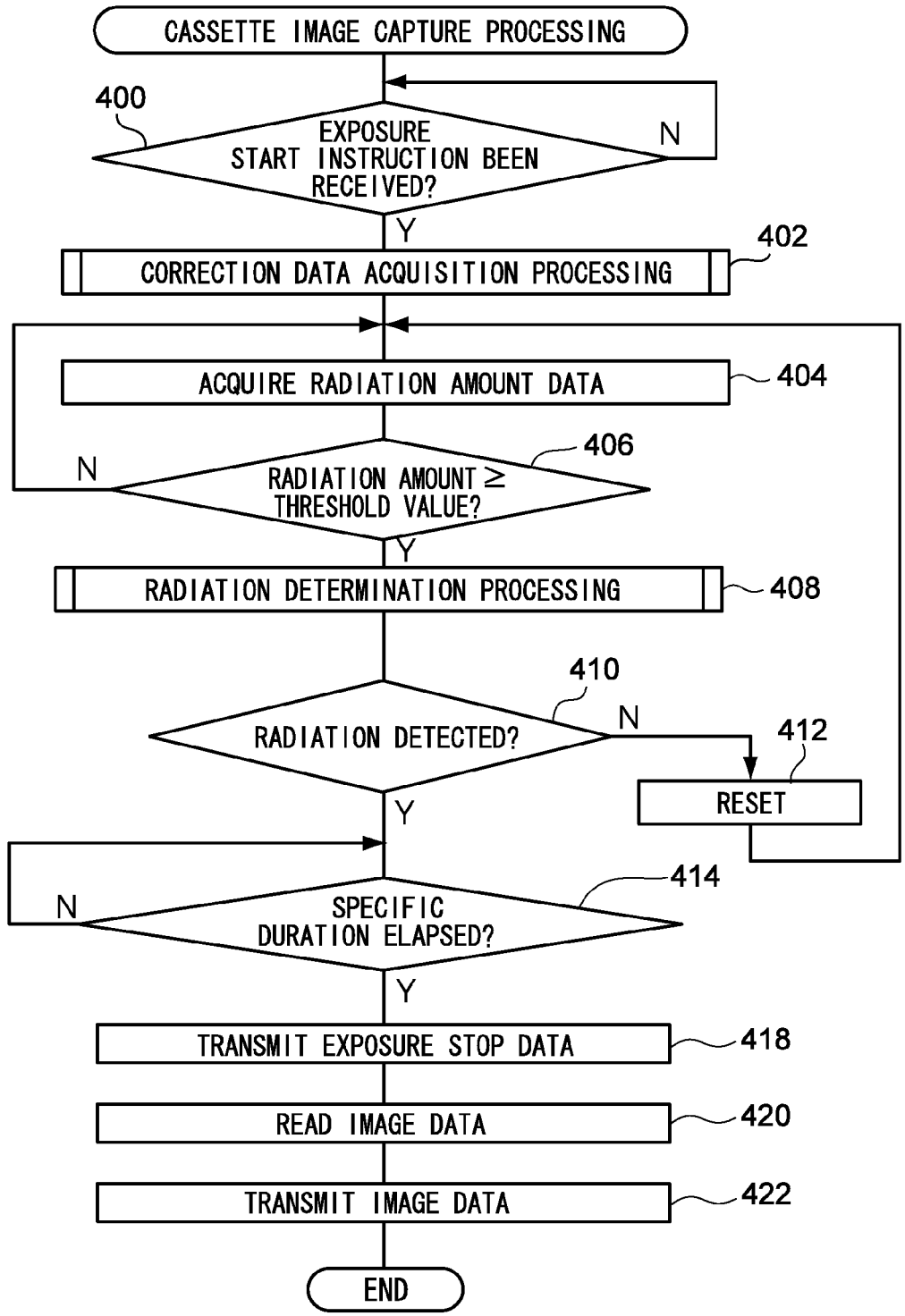
FIG. 16 is a flow chart illustrating flow of processing of a cassette image capture program according to an exemplary embodiment.

Explanation follows regarding operation of the electronic cassette 40 after receiving the initial data from the console 110, with reference to FIG. 16. FIG. 16 is a flow chart illustrating a flow of processing in a cassette image capture processing program executed at this stage by the CPU 58A in the cassette controller 58 of the electronic cassette 40. The program is installed in a specific region of the memory 58B.

At step 400 in FIG. 16, the cassette controller 58 stands by for reception of the instruction data from the console 110 instructing initiation of exposure, and at the next step 402, executes a correction data acquisition processing routine program.

Figure 17:
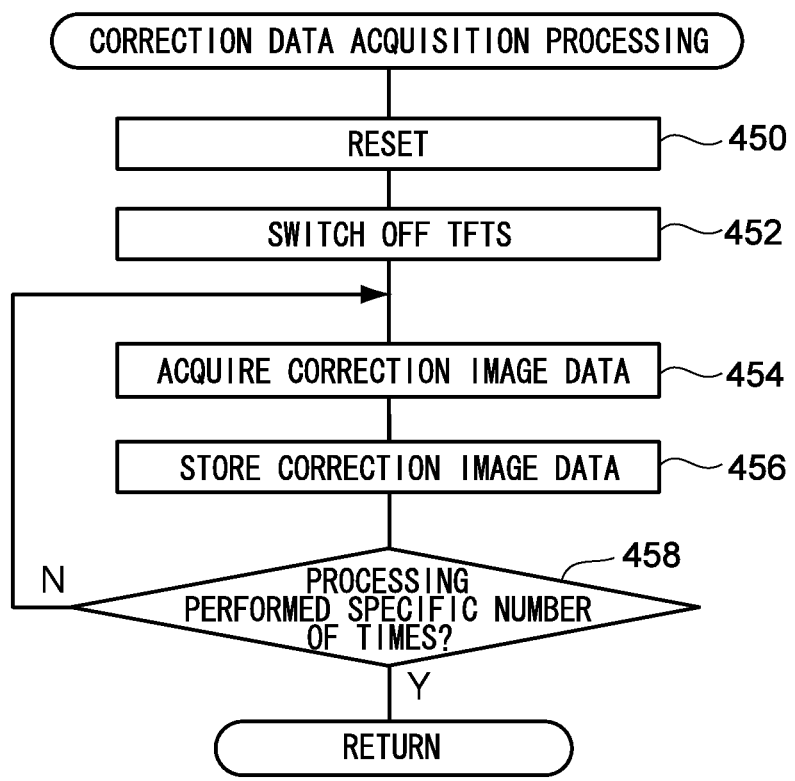
FIG. 17 is a flow chart illustrating a flow of processing in a correction data acquisition processing routine program according to an exemplary embodiment.

Explanation follows regarding the correction data acquisition processing routine program according to the present exemplary embodiment, with reference to FIG. 17. FIG. 17 is a flow chart illustrating a flow of processing of the correction data acquisition processing routine program. The program is installed in a specific region of the memory 58B.

At step 450 in FIG. 17, the cassette controller 58 controls the gate line driver 52 to switch ON all the thin-film transistors 10 in order to reset the radiation detector 20. At the next step 452, the gate line driver 52 controls to switch OFF all the thin-film transistors 10.

At the next step 454, the cassette controller 58 acquires image data based on electric charge read from one of the signal lines 36B (referred to below as "correction detection line image data") by reading from the image memory 56.

Then at the next step 456, the acquired correction detection line image data is stored in a specific region of the memory 58B.

At the next step 458, the cassette controller 58 determines whether or not the processing of the above step 454 to step 456 has been performed n times. If negative determination is made, processing returns to step 454. If affirmative determination is made, the correction data acquisition processing routine program is ended. During the processing of step 454 to step 458 being repeatedly executed, the cassette controller 58 stores at step 456 the correction detection line image data acquired every time in different storage regions, respectively, so that the time sequence of the acquired correction direction detection line image data can be identified.

The correction data acquisition processing routine program is a program to acquire data (correction detection line image data) to be used in offset correction processing to reduce the influence of electric charges due to dark current that occurs in the radiation detector 20 and to reduce the influence of switching noise that occurs when the thin-film transistors 10 are switched, and in fixed noise reduction correction processing to reduce the influence of fixed noise that inherently occurs according to the array position of the respective pixels 32, which are processing performed in a radiation determination processing routine program (FIG. 18) described later.

In the radiation determination processing routine program, as described below, the ratio R is computed based on a set of the radiation detection image data that has been sampled n times from the start point when all the thin-film transistors 10 are switched OFF. Hence, when the processing of step 454 to step 458 of the correction data acquisition processing routine program is repeatedly executed, the timings at which the detection line image data are acquired by the processing of step 454 are set to be substantially the same timing, when acquiring the radiation detection image data in the radiation determination processing routine program, from the start point at which all of the thin-film transistors 10 are switched OFF.

When the correction data acquisition processing routine program is ended, processing returns to step 404 of the cassette image capture processing program (main routine). At step 404, after the cassette controller 58 causes the gate line driver 52 switch ON all of the thin-film transistors 10, the image data that is accordingly stored in the image memory 56 (radiation detection image data) is read and combined to acquire data representing the radiation amount (referred to below as "radiation amount data").

At the next step 406, the cassette controller 58 determines whether or not the radiation amount expressed by the radiation amount data acquired by the processing of step 404 is equal to or greater than the threshold. If negative determination is made, processing returns to step 404. However, if affirmative determination at step 406 is made, it is regarded that the radiation X exposure from the radiation source 121 has started, and processing transitions to step 408.

At step 408, the cassette controller 58 executes the radiation determination processing routine program.

Figure 18:
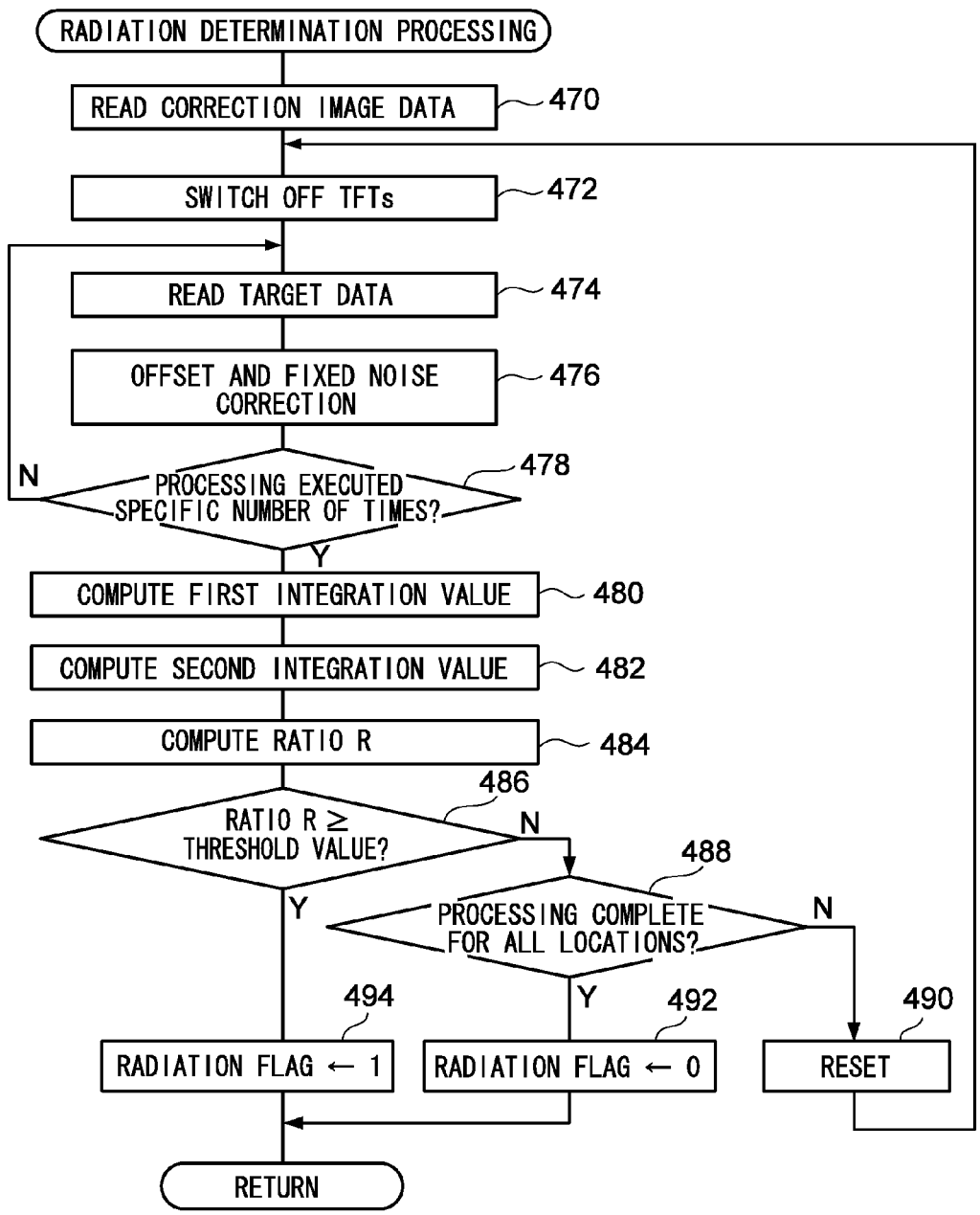
FIG. 18 is flow chart illustrating a flow of processing in a radiation determination processing routine program according to an exemplary embodiment.

Explanation follows regarding the radiation determination processing routine program according to the present exemplary embodiment, with reference to FIG. 18. FIG. 18 is a flow chart illustrating a flow of processing of the radiation determination processing routine program. The program is installed in a specific region of the memory 58B.

At step 470 in FIG. 18, the cassette controller 58 reads the correction detection line image data from the memory 58B.

At the next step 472, the cassette controller 58 controls the gate line driver 52 such that all of the thin-film transistors 10 are switched OFF.

At the next step 474, the cassette controller 58 reads the image data obtained from the signal line 36B corresponding to the any one of the detection pixel lines Ls1, Ls2, Ls3 (referred to below as target detection image data) from the image memory 56.

At the next step 476, the cassette controller 58 subtracts the correction detection line image data from the target detection image data, thereby performing offset correction processing and fixed noise reduction correction processing. The modified target detection image data is stored in a specific region of the memory 58B.

At the next step 478, the cassette controller 58 determines whether or not the processing of step 474 to step 476 has been executed n times. If negative determination is made, processing returns to step 474, and if affirmative determination is made, processing transitions to step 480. When the processing of step 474 to step 478 is being executed repeatedly, the above subtractions are performed at step 476 by using the correction detection line image data obtained at substantially the same timings with the target detection image data, from the start point at which all of the thin-film transistors 10 are switched OFF.

At step 480, the cassette controller 58 reads from the memory 58B all of the set of target detection image data stored as a result of the processing of step 476, and computes the first integration value S1 according to Equation (1). Then at step 482, the second integration value S2 is computed according to Equation (2), and at step 484 the ratio R is computed by substituting the first integration value S1 and the second integration value S2 obtained by the above processing into Equation (3).

In the present exemplary embodiment, the data to be integrated in the processing of step 480 and step 482 are limited to data that fall within a predetermined range. However, embodiments are not limited thereto, and data used in the processing of step 480 and step 482 may not be limited to such range. Examples of the predetermined range include a range defined by fixed values according to various conditions such as the type of radiation detector 20 employed or the operating environment temperature, or a range in a histogram representing the frequency of each image data value, which can be derived from the target detection image data, excluding values separated from the central value by a specific value or greater.

At the next step 486 the cassette controller 58 determines whether or not the ratio R is equal to or greater than a predetermined threshold value (referred to below as "radiation detection threshold value"). If negative determination is made, processing transitions to step 488, and determination is made as to whether or not processing of step 486 has been completed for all of the detection pixel lines Ls1, Ls2, Ls3. If negative determination is made, Processing transitions to step 490 at which the radiation detector 20 is reset by controlling the gate line driver 52 to switch ON all of the thin-film transistors 10, and then processing returns to step 472. However, if affirmative determination is made processing transitions to step 492. Note that when the processing of step 472 to step 490 is repeated, one of the detection pixel lines Ls1, Ls2, Ls3 that has not already been subject to processing is employed in step 474.

The radiation detection threshold value is a value to discriminate between the ratio R under a state not imparted with shock or extraneous noise and the ratio R under in a state imparted with shock or extraneous noise, which can be obtained by tests performed in advance using a real device of the electronic cassette 40, or by, for example, computer simulation based on such factors as the design specification of the electronic cassette 40.

At step 492, the cassette controller 58 sets a value representing determination that radiation has not been detected ("0" in the present exemplary embodiment) to a radiation flag representing whether or not radiation has been detected, and then the radiation determination processing routine program is ended.

However, if affirmative determination is made at step 486, processing transitions to step 494 and the cassette controller 58 sets a value representing determination that radiation has been detected ("1" in the present exemplary embodiment) to the radiation flag. The radiation determination processing routine program is then ended.

When the radiation determination processing routine program is ended, processing returns to step 410 of the cassette image capture processing program (main routine).

At step 410, the cassette controller 58 determines whether or not it is determined in the radiation determination processing routine program that radiation has been detected by referring to the value of the radiation flag. If negative determination is made, it is regarded that any detection made was due to the influence of shock or extraneous noise, and processing transitions to step 412. At step 412, the gate line driver 52 is controlled so as to switch ON all of the thin-film transistors 10 and reset the radiation detector 20, and thereafter processing returns to step 404. However, if affirmative determination is made at step 410, processing transitions to step 414.

At step 414, the cassette controller 58 waits for a predetermined duration to elapse as an appropriate imaging duration according to such factors as the imaging target site and the imaging conditions. At the next step 418, the exposure stop data is transmitted to the console 110 using the wireless communication unit 60.

At the next step 420, the cassette controller 58 controls the gate line driver 52 such that an ON signal is output in sequence one line at a time from the gate line driver 52 to each of the gate lines 34, thereby switching ON each of the thin-film transistors 10 connected to each of the gate lines 34 one line at a time.

In the radiation detector 20, after each of the thin-film transistors 10 connected to each of the gate lines 34 is switched ON in sequence one line at a time, the electric charges that have been accumulated in the capacitors 9 flow out of the respective signal line 36 as electrical signals, one line at a time. The electrical signals that flow out of each of the signal lines 36 are converted into digital image data by the signal processor 54, and stored in the image memory 56.

The cassette controller 58 thus reads image data stored in the image memory 56 at step 420, and at the next step 422, the read image data is transmitted to the console 110 using the wireless communication unit 60. Thereafter, the cassette image capture processing program is ended.

In the electronic cassette 40 according to the present exemplary embodiment, as illustrated in FIG. 8, the radiation detector 20 is installed in a state such that the radiation X is irradiated from the TFT substrate 30 side.

Figure 19:
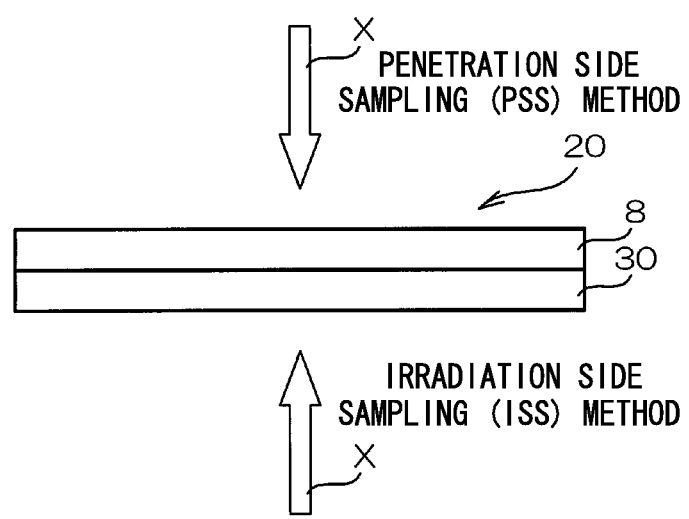
FIG. 19 is a cross-sectional side view for explaining radiographic imaging using an Irradiation Side Sampling (ISS) method and a Penetration Side Sampling (PSS) method.

In this regard, as shown in FIG. 19, in a case in which the radiation detector 20 is configured to achieve a Penetration Side Sampling (PSS) method, in which the radiation detector 20 is irradiated with radiation from the side at which the scintillator 8 is formed and radiographic images are read by the TFT substrate 30 provided on the back side of the radiation incident face, light is emitted with higher intensity at the face of the scintillator 8 on the top side in FIG. 19 (the opposite side to the TFT substrate 30 side). However, in a case in which the radiation detector 20 is configured to achieve an Irradiation Side Sampling (ISS) method, in which the radiation detector 20 is irradiated with radiation from the TFT substrate 30 side and a radiographic image is read by the TFT substrate 30 provided on the radiation incident face side, since radiation that has passed through the TFT 30 is incident to the scintillator 8, light is emitted with higher intensity from the TFT substrate 30 side of the scintillator 8. Each of the sensor portions 13 provided to the TFT substrate 30 generates electric charges due to the light generated by the scintillator 8. Therefore, the radiation detector 20 gives a higher resolution of captured radiographic images in cases in which an ISS method is employed than cases in which a PSS method is employed, since the most intense light emission position of the scintillator 8 is closer to the TFT substrate 30.

The radiation detector 20 is configured with the photoelectric conversion layer 4 formed from an organic photoelectric conversion material and so radiation is barely absorbed by the photoelectric conversion layer 4. Therefore, even if the radiation detector 20 according to the present exemplary embodiment employs an ISS method, since the amount of radiation absorbed by the photoelectric conversion layer 4 is low even through radiation passes through the TFT substrate 30, drop in sensitivity to radiation can prevented. In an ISS method, radiation reaches the scintillator 8 after passing through the TFT substrate 30. However, the configuration in which the photoelectric conversion layer 4 of the TFT substrate 30 is formed by an organic photoelectric conversion material is suitable for an ISS method since hardly any radiation is absorbed in the photoelectric conversion layer 4 and radiation attenuation is reduced to a small amount.

It is possible to form both the amorphous oxide material configuring the active layer 17 of the thin-film transistors 10 and the organic photoelectric conversion material configuring the photoelectric conversion layer 4 into a film at low temperature. Therefore, the substrate 1 can accordingly be formed from plastic resin, aramid and/or bionanofibers, having low absorptivity to radiation. Since the amount of radiation absorbed by the thus formed substrate 1 is small, sensitivity to radiation can be prevented from falling even if an ISS method is employed and radiation passes through the TFT substrate 30.

As illustrated in FIG. 8, the radiation detector 20 of the present exemplary embodiment is affixed to the top plate 41B inside the housing 41 such that the TFT substrate 30 is on the top plate 41B side. In this case, if the substrate 1 is formed from a high rigidity plastic resin, aramid and/or bionanofibers, since the rigidity of the radiation detector 20 itself is high, the top plate 41B of the housing 41 can be formed thinner. Further, if the substrate 1 is formed from a high rigidity plastic resin, aramid and/or bionanofibers, since the radiation detector 20 itself is flexible, the radiation detector 20 is not readily damaged even if shock is imparted to the imaging region 41A.

As explained in detail above, in the present exemplary embodiment, the first integration value is obtained by integrating values expressed by a signal output from a radiation detection sensor (the detection pixels 32A) over a predetermined period of time, and the second integration value is obtained by integrating change amounts per specific time duration in values expressed by a signal output from the sensor over the predetermined period of time. Then determination is made as to whether or not radiation has been detected by the sensor based on a ratio of the first integration value and the second integration value. Accordingly, radiation detection can be performed with high precision irrespective of the irradiation amount of radiation.

Moreover, in the present exemplary embodiment, since it is determined that radiation has been detected by the sensor if the ratio of the first integration value to the second integration value is equal to or greater than a predetermined threshold value, the radiation detection can be performed simply.

In the present exemplary embodiment, the sensor includes conversion portions (the photoelectric conversion layer 4 and the scintillator 8) that convert irradiated radiation into electric charges, and switching elements (the thin-film transistors 10) that is switched ON to read out the electric charges generated by the conversion portions. Off-set correction is also performed on the first integration value and the second integration value to reduce the influence of electric charges arising due to dark current occurring in the conversion portion and/or switching noise that occurs when the switching elements are switched. Consequently, radiation detection can be performed with higher precision.

Moreover, radiation can be detected at higher precision in the present exemplary embodiment since fixed noise reduction correction is performed on the first integration value and the second integration value to reduce the influence of fixed noise that inherently occurs according to the array position in the sensor.

In the present exemplary embodiment, the values subject to integration in the first integration value and the second integration value are values that fall within a predetermined range. As a result, influence from such factors as unexpected noise can be reduced, and radiation irradiation can be detected with higher precision.

Since the sensor of the present exemplary embodiment is provided in a radiographic image capture panel (the radiation detector 20), a region is not required to provide the above sensor at another position.

In the present exemplary embodiment, the sensor is configured as radiation detection pixels each including a conversion portion, and the radiographic image capture panel includes the radiographic image capture pixels and the radiation detection pixels that are arrayed in a matrix formation, in which a line (array) including the radiation detection pixels is included, and includes plural signal lines that are respectively connected to pixels arrayed in a different one of the line. Values expressed by electric charges read from the signal line for the line including the radiation detection pixels are integrated, and amounts of change per specific time duration in values expressed by electric charges read from the signal line for the line including the radiation detection pixels are integrated. Accordingly, the present invention can be readily implemented using existing radiographic image capture panels.

Moreover, since the sensor of in the present exemplary embodiment includes the switching element that has been shorted across the switching terminals, the sensor can be easily configured using existing manufacturing processes.

Although explanation of an exemplary embodiment has been given above, the technical scope of the present invention is not limited the above exemplary embodiment. Various modifications and improvements may be made to the above exemplary embodiment within a scope not departing from the spirit of the present invention, and such modifications and improvements fall within the technical scope of the present invention.

The above exemplary embodiment does not limit the invention as recited in the claims, and not all of the combinations of the components explained in the above exemplary embodiment are required to realize the solution of the invention. The above exemplary embodiment includes various levels of invention, and various aspects of the invention can be obtained by suitably combining part of the components described above. As long as the advantageous effect can be obtained, even if a number of the components are omitted from the total configuration described in the exemplary embodiment, any such configuration may fall within the scope of the invention.

For example, explanation has been given in the above exemplary embodiment in which, after detection of initiation of radiation irradiation, determination is made by the radiation determination function as to whether or not the detected value indicates radiation. However, exemplary embodiments are not limited thereto and, for example, an embodiment may be configured such that the initiation of radiation irradiation is also detected by the radiation determination function. Such an embodiment may be configured by omitting the processing of step 404 and step 406 from the cassette image capture processing program (see FIG. 16). Such a case enables faster detection of initiation of radiation irradiation than in the above exemplary embodiment, and processing can be simplified.

In the above exemplary embodiment, explanation has been given of an example in which image data for offset correction and image data for fixed noise reduction correction is acquired at the same time by acquiring combined image data of one lines worth of the signal lines 36 as the image data for use in the radiation determination function. However, exemplary embodiments are not limited thereto, and for example an embodiment may be configured in which only a portion of each of the above image data is acquired in order to realize faster processing. In such cases, image data for performing offset correction and image data for performing fixed noise reduction correction may be acquired separately as the correction detection line image data acquired by the correction data acquisition processing routine program, and the offset correction and the fixed noise reduction correction performed separately using respective data.

Explanation has been given of a case in the above exemplary embodiment in which the detection pixels 32A are configured by the thin-film transistors 10 with shorted source and drain; however, exemplary embodiments are not limited thereto. For example, an embodiment may be configured in which the detection pixels 32A is formed by directly connecting a dedicated signal line for radiation detection to the connection portion between the respective capacitors 9 and the thin-film transistors 10.

Figure 20A:
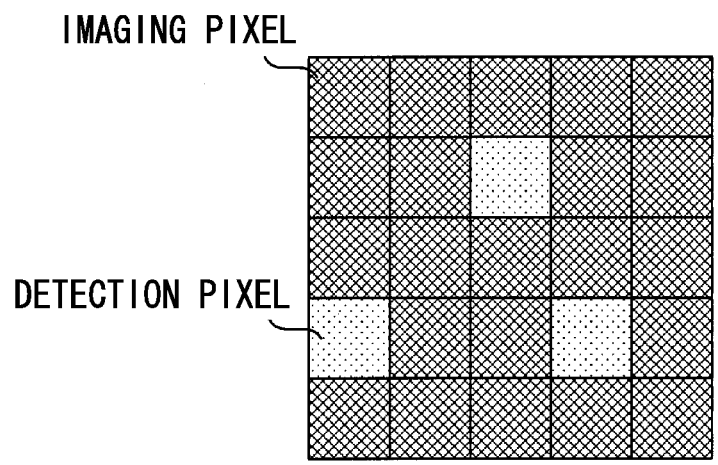
FIG. 20A and FIG. 20B are plan views illustrating examples of alternative configurations of a radiation detector according to an exemplary embodiment.
Figure 20B:
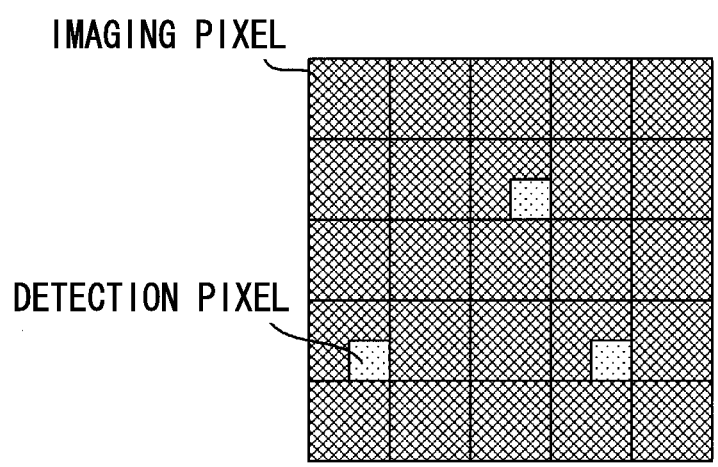

Explanation has been given of a case in the above exemplary embodiment in which, as shown in the example in FIG. 20A, a portion of the imaging pixels 32B are applied as the detection pixels 32A. However, exemplary embodiments are not limited thereto. For example, as shown in the example in FIG. 20B, an embodiment may be configured in which the detection pixels 32A are provided in spaces between the imaging pixels 32B. In such cases, although there is a reduction in the surface area of the imaging pixels 32B in the positions at which the detection pixels 32A are provided, leading to a drop in sensitivity in those pixels, since these detection pixels 32B can also be employed for radiographic image detection, the quality of radiographic images can be increased.

There is also no requirement to apply the pixels of the radiation detector 20 as a sensor for radiation detection. For example, an embodiment may be configured in which a dedicated sensor for radiation detection that generates electric charges when radiation is irradiated is provided at a predetermined position in the radiation detector 20, such as between each pixel array or at peripheral edge portions, and determination is made as to whether or not radiation has been detected by using the ratio R based on the values obtained from this sensor. In such cases, the sensor does not necessarily have to be provided to the radiation detector 20, and may be disposed separately to the radiation detector 20.

Explanation has been given in the above exemplary embodiment of a case in which the detection pixels 32A are provided separately to the imaging pixels 32B. However, exemplary embodiments are not limited thereto, and an embodiment may be configured in which the detection pixels 32A are not provided, and the imaging pixels 32B are applied as a sensor for determining whether or not radiation has been detected, that is to say, an embodiment in which the imaging pixels 32B are shared as the sensor. In such cases, there is no need to provide additional sensors, and the radiation detector 20 can be readily implemented.

Explanation has been given in the above exemplary embodiment of a case in which the ratio R illustrated by Equation (3) is applied as the ratio. However, exemplary embodiments are not limited thereto, and for example, an embodiment may be configured with a ratio obtained by a computation equation in which the top and bottom of Equation (3) are interchanged is applied as the ratio. In such cases, radiation detection is determined if the ratio is smaller than a predetermined threshold value.

Moreover, there is no limitation to embodiments such as the above wherein the first integration value and the second integration value are applied as they are to compute the ratio. For example, an embodiment is possible in which the first integration value and/or the second integration value are multiplied by predetermined weighting values.

Moreover, explanation has been given in the above exemplary embodiment of a case in which the sensor portions 13 are formed of an organic photoelectric conversion material that generates electric charges on receipt of light generated by the scintillator 8. However, exemplary embodiments are not limited thereto, and an embodiment may be configured by applying sensor portions 13 that do not containing an organic photoelectric conversion material.

Explanation has been given in the above exemplary embodiment of a case in which the case 42 for housing the cassette controller 58 and the power supply section 70 inside the housing 41 of the electronic cassette 40 is disposed so as not to overlap with the radiation detector 20; however, there is no limitation thereto. For example, the cassette controller 58 and/or the power supply section 70 may be disposed so as to overlap with the radiation detector 20.

Explanation has been given in the above exemplary embodiment of a case in which wireless communication is performed between the electronic cassette 40 and the console 110 and between the radiation generator 120 and the console 110. However, the exemplary embodiments are not limited thereto and, for example, an embodiment may be configured in which wired communication performed between one or both of these pairs.

While explanation has been given in the above exemplary embodiment of a case in which X-rays are applied as the radiation, the present invention is not limited thereto. An embodiment may be applied with other types of radiation, such as gamma radiation.

In addition, the configuration of the RIS 100 (see FIG. 1), the configuration of the radiographic imaging room (see FIG. 2), the configuration of the electronic cassette 40 (see FIG. 3 to FIG. 8) and the configuration of the imaging system 104 (see FIG. 9) explained in the above exemplary embodiment are merely examples thereof. Parts not required may be omitted, additional parts may be added and connection states changed within a scope not departing from the spirit of the present invention.

Moreover, the flow of processing in each of the programs explained in the above exemplary embodiment (see FIG. 14 and FIG. 16 to FIG. 18) are merely examples thereof. Steps not required may be omitted, new steps may be added, and the processing sequence may be switched around within a scope not departing from the spirit of the present invention.

What is claimed is:

1. A radiation detection device comprising:
a sensor that detects radiation;
an electronic cassette comprising a controller, the controller including:
a first integration section executed by the controller and being configured to obtain a first integration value by integrating values expressed by signals output from the sensor over a predetermined period of time;
a second integration section executed by the controller and being configured to obtain a second integration value by integrating amounts of change per specific time duration in values expressed by the signals output from the sensor over the predetermined period of time; and
a determination section executed by the controller and being configured to determine whether or not radiation has been detected by the sensor based on a ratio of the first integration value to the second integration value.

2. The radiation detection device of claim 1, wherein the determination section is configured to determine that radiation has been detected by the sensor if the ratio of the first integration value to the second integration value is equal to or greater than a threshold value.

3. The radiation detection device of claim 1, wherein:
the sensor comprises a conversion portion that converts irradiated radiation into electric charge and a switching element that is switched ON when reading electric charge generated by the conversion portion;
the radiation detection device further comprises an offset correction section configured to perform offset correction on the first integration value and the second integration value to reduce one or more of the influence of electric charge arising from dark current occurring in the conversion portion or the influence of switching noise that occurs when the switching element is switched; and
the determination section is configured to perform the determination using the first integration value and the second integration value on which the offset correction has been performed.

4. The radiation detection device of claim 1, further comprising a fixed noise correction section configured to perform fixed noise reduction correction on the first integration value and the second integration value to reduce the influence of fixed noise that inherently occurs according to a position of the sensor,
wherein the determination section is configured to perform the determination using the first integration value and the second integration value on which the fixed noise reduction correction has been performed.

5. The radiation detection device of claim 1, wherein the values subject to integration by the first integration section and the second integration section are values within a predetermined range.

6. A radiographic image capture device comprising:
the radiation detection device of claim 1;

a radiographic image capture panel including a plurality of radiographic image capture pixels, each including a conversion portion that converts irradiated radiation into electric charge and a switching element that is switched ON when reading electric charge generated by the conversion portion, wherein the controller being configured to control the radiographic image capture panel to perform radiographic image capture if it is determined by the determination section of the radiation detection device that radiation has been detected by the sensor.

7. The radiographic image capture device of claim 6, wherein the sensor of the radiation detection device is provided at the radiographic image capture panel.

8. The radiographic image capture device of claim 7, wherein:

the sensor comprises a plurality of radiation detection pixels, each including the conversion portion;

the radiographic image capture panel comprises: the plurality of radiographic image capture pixels and the plurality of radiation detection pixels arrayed in a matrix formation, the matrix formation comprising a plurality of arrays including an array that includes at least one of the radiation detection pixels; and a plurality of signal lines, each of which is connected to the pixels arrayed in a different one of the plurality of arrays;

the first integration section is configured to integrate values, representing electric charge read from a signal line of the plurality of signal lines provided for the array that includes at least one of the radiation detection pixels, as the first integration value; and the second integration section is configured to integrate amounts of change per specific time duration in values, representing electric charge read from the signal line of the plurality of signal lines provided for the array that includes at least one of the radiation detection pixels, as the second integration value.

9. The radiographic image capture device of claim 7, wherein a portion of the plurality of radiographic image capture pixels is used as the sensor.

10. The radiographic image capture device of claim 7, wherein the switching element of the sensor is shorted across switching terminals.

11. A radiation detection method including an electronic cassette comprising a controller, the method comprising:

acquiring, via the controller, a first integration value by integrating values expressed by signals output from a sensor for radiation detection over a predetermined period of time;

acquiring, via the controller, a second integration value by integrating amounts of change per specific time duration in values expressed by the signals output from the sensor over the predetermined period of time; and determining, via the controller, whether or not radiation has been detected by the sensor based on a ratio of the first integration value to the second integration value.

12. A non-transitory storage medium stored with a program that causes a computer to execute radiation detection processing including an electronic cassette comprising a controller, the radiation detection processing comprising:

acquiring, via the controller, a first integration value by integrating values expressed by signals output from a sensor for radiation detection over a predetermined period of time;

acquiring, via the controller, a second integration value by integrating amounts of change per specific time duration in values expressed by the signals output from the sensor over the predetermined period of time; and determining, via the controller, whether or not radiation has been detected by the sensor based on a ratio of the first integration value to the second integration value.

13. The radiographic image capture device of claim 6, further comprising an image memory into which radiographic image data of a radiographic image obtained by the radiographic image capture panel is stored.

14. The radiographic image capture device of claim 13, wherein the image memory is configured to store radiographic image data for a predetermined number of frames worth of radiographic images.

15. The radiographic image capture device of claim 6, wherein the radiographic image capture device comprises a portable radiographic image capture device.

16. The radiographic image capture device of claim 6, further comprising a built-in battery coupled to the radiation detection device.

17. The radiographic image capture device of claim 6, further comprising a wireless communication unit configured to perform wireless communication with an external device.

* * * * *